(12) United States Patent
Eto et al.

(10) Patent No.: US 10,947,504 B2
(45) Date of Patent: Mar. 16, 2021

(54) METHOD FOR PRODUCING HIGHLY FUNCTIONAL PLATELETS

(71) Applicants: Kyoto University, Kyoto (JP); Megakaryon Corporation, Kyoto (JP)

(72) Inventors: Koji Eto, Kyoto (JP); Sou Nakamura, Kyoto (JP); Yukitaka Ito, Kyoto (JP); Tomohiro Shigemori, Kyoto (JP); Takeaki Dohda, Kyoto (JP)

(73) Assignees: Kyoto University, Kyoto (JP); Megakaryon Corporation, Kyoto (JP)

( * ) Notice: Subject to any disclaimer, the term of this patent is extended or adjusted under 35 U.S.C. 154(b) by 91 days.

(21) Appl. No.: 15/735,685

(22) PCT Filed: Jun. 16, 2016

(86) PCT No.: PCT/JP2016/068015
§ 371 (c)(1),
(2) Date: Dec. 12, 2017

(87) PCT Pub. No.: WO2016/204256
PCT Pub. Date: Dec. 22, 2016

(65) Prior Publication Data
US 2019/0048317 A1    Feb. 14, 2019

(30) Foreign Application Priority Data
Jun. 16, 2015 (JP) .............................. JP2015-121456

(51) Int. Cl.
| | |
|---|---|
| *C12N 5/078* | (2010.01) |
| *A61K 31/553* | (2006.01) |
| *A61K 35/19* | (2015.01) |
| *A61K 31/551* | (2006.01) |
| *C12N 5/077* | (2010.01) |
| *C12N 15/113* | (2010.01) |
| *C12N 15/09* | (2006.01) |

(52) U.S. Cl.
CPC .......... *C12N 5/0644* (2013.01); *A61K 31/551* (2013.01); *A61K 31/553* (2013.01); *A61K 35/19* (2013.01); *C12N 5/0669* (2013.01); *C12N 15/09* (2013.01); *C12N 15/113* (2013.01)

(58) Field of Classification Search
None
See application file for complete search history.

(56) References Cited

U.S. PATENT DOCUMENTS

| | | | |
|---|---|---|---|
| 2010/0120750 A1* | 5/2010 | Crispino | A61K 31/5513 514/218 |
| 2012/0238020 A1 | 9/2012 | Beau et al. | |
| 2014/0050711 A1* | 2/2014 | Murphy | C12N 5/0644 424/93.72 |
| 2014/0127815 A1* | 5/2014 | Eto | C12N 5/0644 435/467 |

FOREIGN PATENT DOCUMENTS

| | | |
|---|---|---|
| WO | 2012157586 A1 | 11/2012 |
| WO | 2014100779 A1 | 6/2014 |
| WO | 2014138485 A1 | 9/2014 |

OTHER PUBLICATIONS

Hagberg et al. Platelets (2000) 11: 137-150 (Year: 2000).*
International Search Report received in PCT/JP2016/068015, dated Aug. 16, 2016.
Written Opinion received in PCT/JP2016/068015, dated Aug. 16, 2016.
Chang et al., "Proplatelet formation is regulated by the Rho/ROCK pathway", May 15, 2007, pp. 4229-4236, vol. 109, No. 10, Publisher: Blood.
European Search Opinion received in EPEP20160811730 dated Nov. 13, 2018.
Supplemental European Search Report received in EPEP20160811730 dated Nov. 13, 2018.
Lindsey et al., "Platelets from mice lacking the aryl hydrocarbon receptor exhibit defective collagen-dependent signaling", Mar. 5, 2014, pp. 383-394, vol. 12, No. 3, Publisher: J Thromb Haemost.
Takayama, et al., "Generation of functional platelets from human embryonic stem cells in vitro via ES-sacs, VEGF-promoted structures that concentrate hematopoietic progenitors", Jun. 1, 2008, pp. 5298-5306, vol. 111, No. 11, Publisher: Blood.
Shaturny, et al., "Activators, receptors and intracellular signaling pathways in blood platelets", 2014, pp. 182-185 (machine translation of English Abstract), vol. 60, No. 2, Publisher: Biomedical Chemistry.
Zimmerman, et al., "Preparation of Highly Concentrated and White Cell-Poor Platelet-Rich Plasma by Plateletpheresis", Jul. 2008, pp. 20-25, vol. 95, No. 1.

* cited by examiner

*Primary Examiner* — James D Schultz
(74) *Attorney, Agent, or Firm* — Suzannah K. Sundby, Esq.; Canady + Lortz LLP

(57) ABSTRACT

The present invention provides a highly functional platelet production promoting agent which comprises one or a plurality of aryl hydrocarbon receptor (AhR) antagonists and one or a plurality of Rho-associated coiled-coil forming kinase (ROCK) inhibitors.

20 Claims, 22 Drawing Sheets
Specification includes a Sequence Listing.

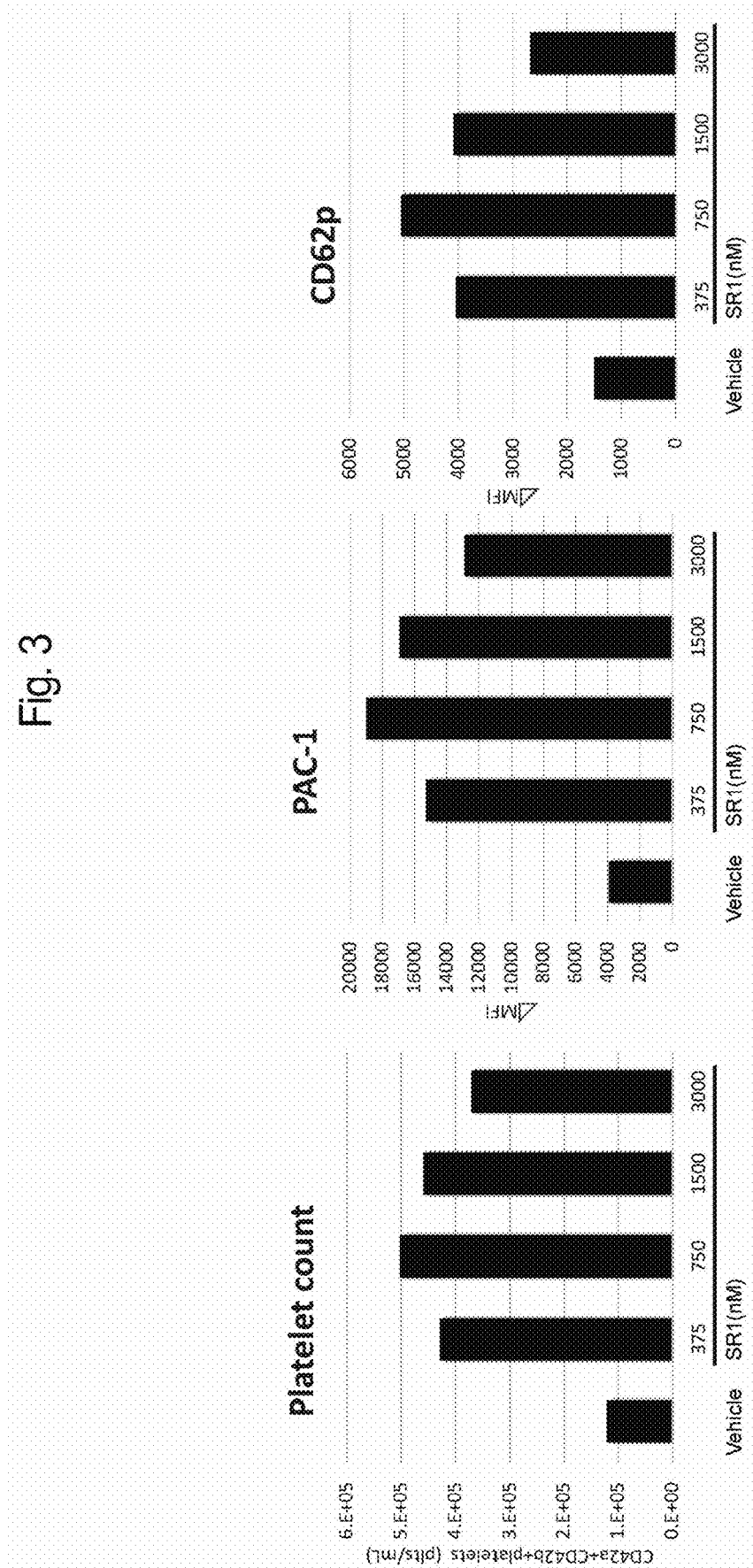

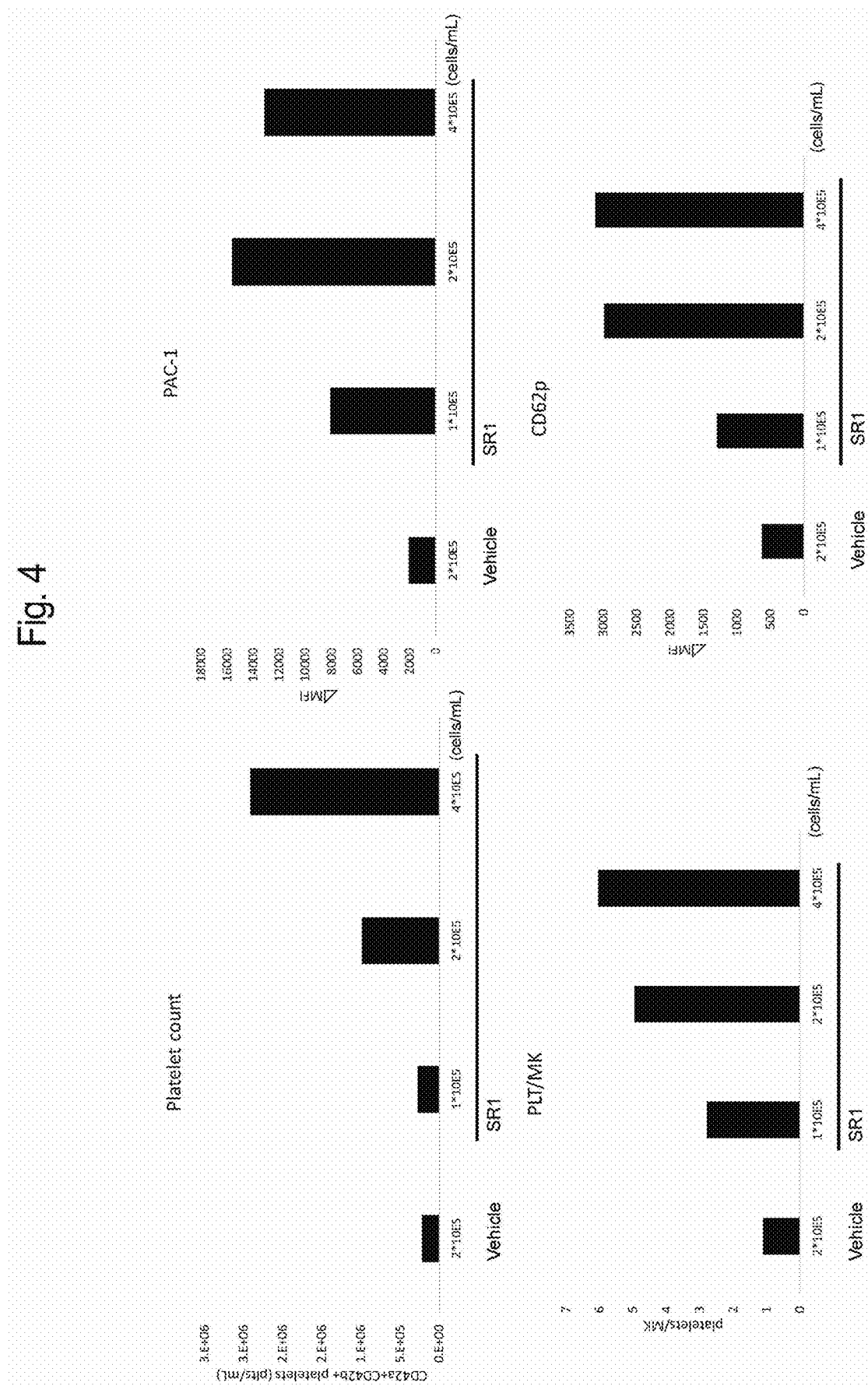

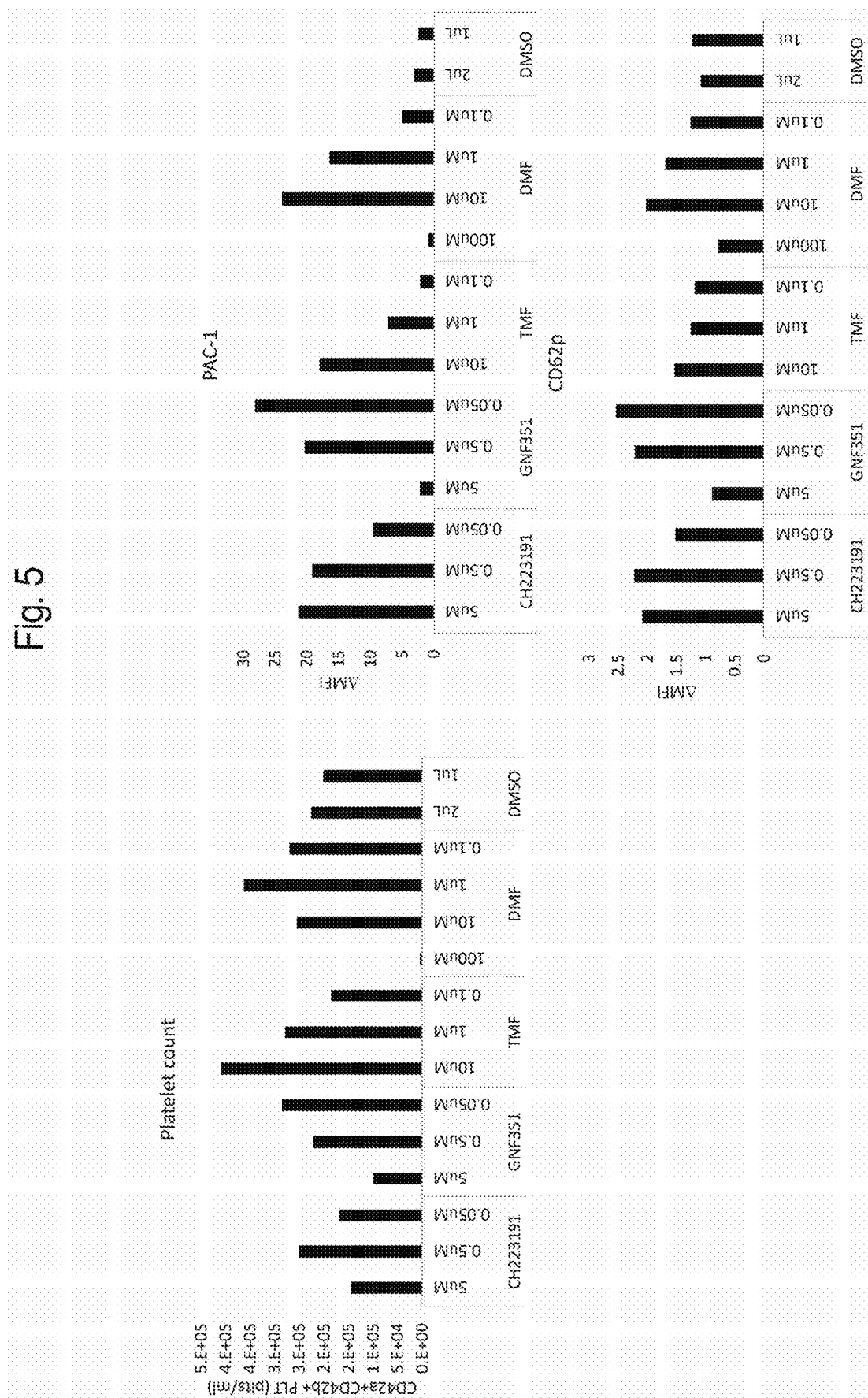

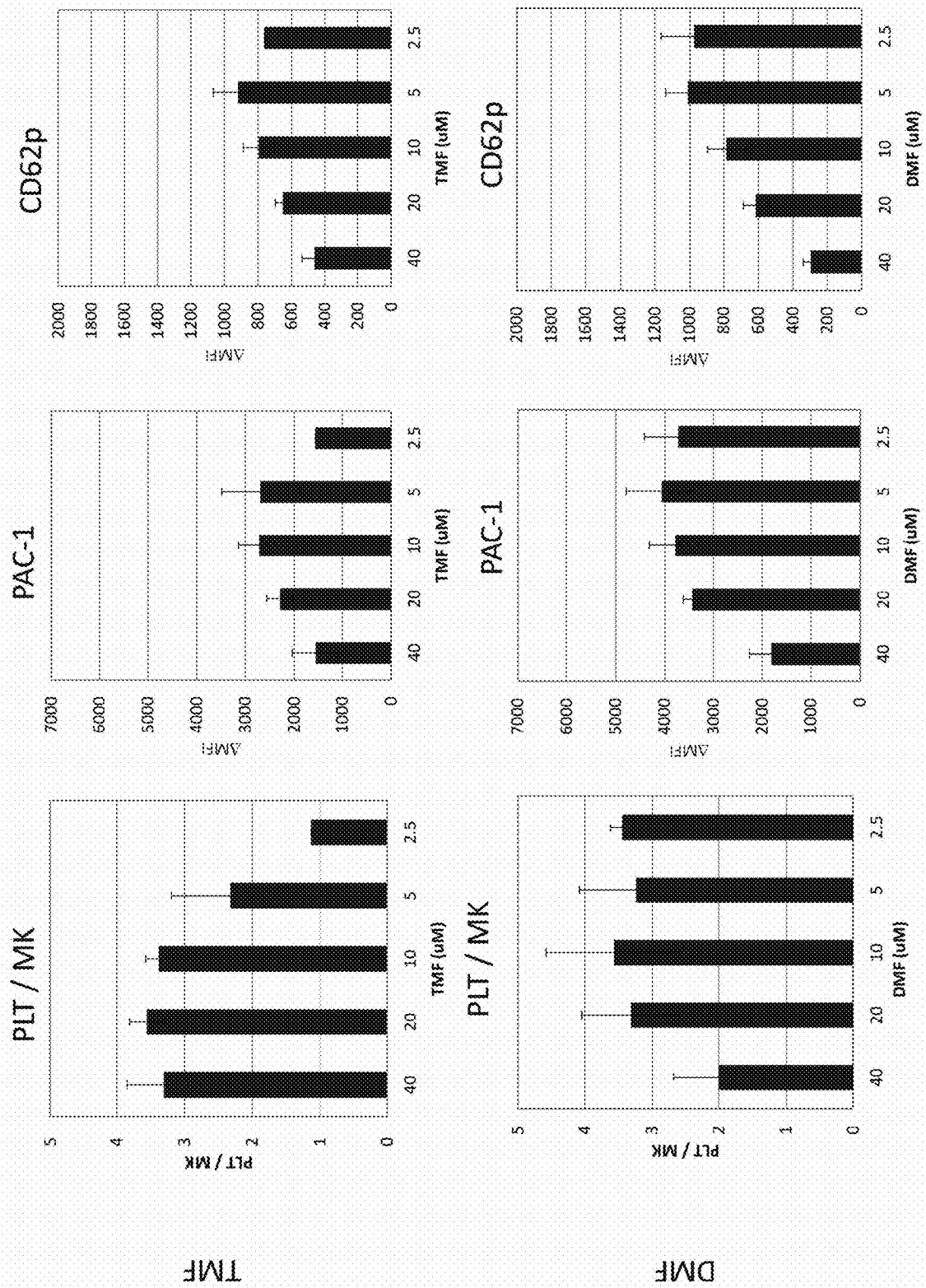

Fig. 15
SR1
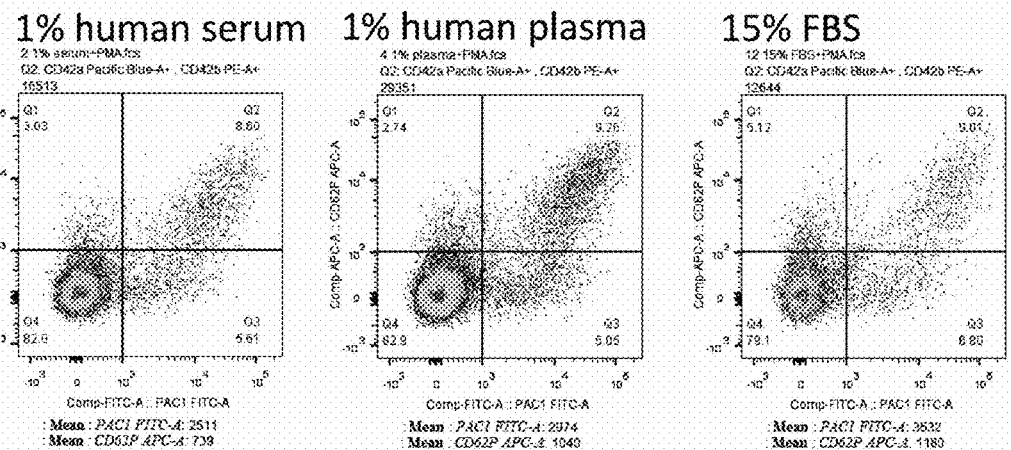
SR1+ Y27632
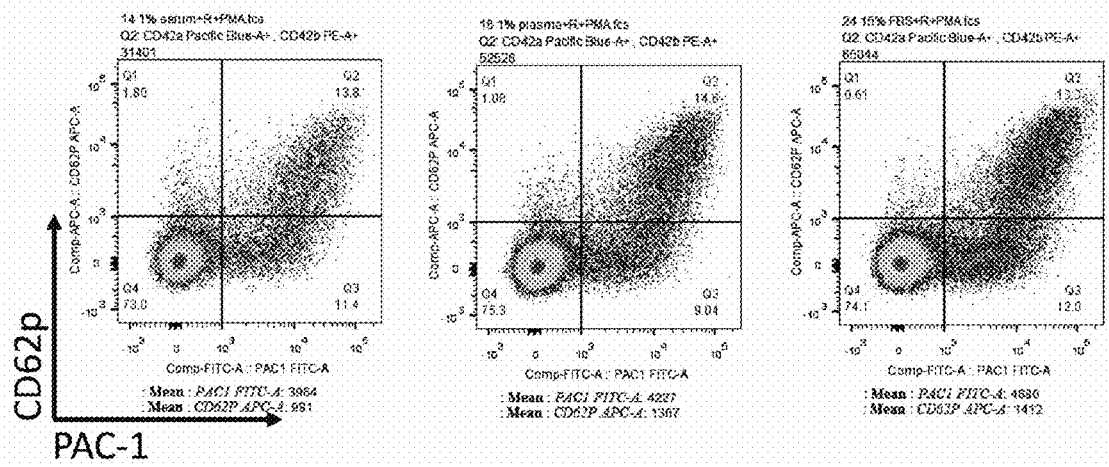
CD62p / PAC-1

SEQUENCE LISTING

```
<160> NUMBER OF SEQ ID NOS: 6

<210> SEQ ID NO 1
<211> LENGTH: 22
<212> TYPE: DNA
<213> ORGANISM: Homo sapiens

<400> SEQUENCE: 1
gaggtcacac tagagagtta ta                                              22

<210> SEQ ID NO 2
<211> LENGTH: 71
<212> TYPE: DNA
<213> ORGANISM: Artificial
<220> FEATURE:
<223> OTHER INFORMATION: Synthesized DNA.

<400> SEQUENCE: 2
gatccccgag gtcacactag agagttatat tcaagagata taactctcta gtgtgacctc     60
tttttggaaa a                                                          71

<210> SEQ ID NO 3
<211> LENGTH: 19
<212> TYPE: DNA
<213> ORGANISM: Homo sapiens

<400> SEQUENCE: 3
actttccagt cgactctca                                                  19

<210> SEQ ID NO 4
<211> LENGTH: 65
<212> TYPE: DNA
<213> ORGANISM: Artificial
<220> FEATURE:
<223> OTHER INFORMATION: Synthesized DNA.

<400> SEQUENCE: 4
gatccccact ttccagtcga ctctcattca agagatgaga gtcgactgga aagttttttg     60
```

```
gaaaa                                                               65

<210> SEQ ID NO 5
<211> LENGTH: 22
<212> TYPE: DNA
<213> ORGANISM: Homo sapiens

<400> SEQUENCE: 5
atgagacgaa atgctgatgt at                                            22

<210> SEQ ID NO 6
<211> LENGTH: 71
<212> TYPE: DNA
<213> ORGANISM: Artificial
<220> FEATURE:
<223> OTHER INFORMATION: Synthesized DNA.

<400> SEQUENCE: 6
gatccccatg agacgaaatg ctgatgtatt tcaagagaat acatcagcat ttcgtctcat   60
tttttggaaa a                                                        71
```

METHOD FOR PRODUCING HIGHLY FUNCTIONAL PLATELETS

REFERENCE TO A SEQUENCE LISTING SUBMITTED VIA EFS-WEB

The content of the ASCII text file of the sequence listing named "20171212_101621_003 US1_seq" which is 1.48 kb in size was created on Dec. 12, 2017 and electronically submitted via EFS-Web herewith the application is incorporated herein by reference in its entirety.

TECHNICAL FIELD

The present invention relates to a method for producing platelets in vitro.

BACKGROUND ART

Hematopoietic cells used for therapeutic applications are required in cases of treating blood-related diseases or in cases of surgical treatment. Among these hematopoietic cells, platelets, which are cells essential for blood coagulation (hemostasis), proplatelets, and megakaryocytes, which are cells that produce platelets, are cells for which there is a particularly high demand. Platelets in particular are in high demand for leukemia, bone marrow transplants, anti-cancer therapy and the like, and there is a strong need for a stable supply thereof.

A method for obtaining megakaryocytes by differentiating various types of stem cells followed by the culturing thereof to release platelets into the medium has previously been developed as a method for producing platelets in vitro. More recently, the usefulness of pluripotent stem cells as an important source for cell therapy in regenerative medicine has attracted even more attention due to the establishment of iPS cells. Takayama, et al., for example, have previously succeeded in inducing human ES cells to differentiate into megakaryocytes and platelets (Non-Patent Document 1).

However, platelets obtained in vitro thus far have been observed to lack the inherent function thereof, namely the ability to coagulate blood.

In addition, conventional methods for producing platelets in vitro have encountered difficulty in obtaining sufficiently functional platelets without using feeder cells. However, since feeder cells frequently use cells derived from species other than humans, it is desirable to not use feeder cells when producing platelets for administration to humans.

One example of a previously proposed method for producing platelets from hematopoietic progenitor cells in vitro includes culturing megakaryocytes in the presence of TPO and an aryl hydrocarbon receptor (AhR) antagonist (Patent Document 1).

CITATION LIST

Patent Documents

Patent Document 1: WO 2014/138485

Non-Patent Documents

Non-Patent Document 1: Takayama, N. et al., Blood, 111, pp. 5298-5306, 2008

SUMMARY

Technical Problem

An object of the present invention is to provide a method for efficiently producing highly functional platelets from megakaryocytes in vitro.

Solution to Problem

As a result of conducting extensive studies to solve the above-mentioned problem, the inventors of the present invention found that, when megakaryocytes are cultured in the presence of an AhR antagonist, the number of platelets produced increases and the function thereof is enhanced, and that, in the case of combining with the use of a ROCK inhibitor, the action thereof is not additive, but synergistic. Culturing conditions for obtaining platelets demonstrating even higher functionality were also examined, thereby leading to completion of the present invention.

Moreover, the inventors of the present invention also found that, by suppressing the expression or function of HMGA proteins, the number of platelets produced per megakaryocyte unit increases. In addition, when these megakaryocytes were perceived visually, they were observed to have become multinucleated and enlarged while also forming a separation membrane and secretory granules, thus indicating that the inventors of the present invention had succeeded in causing the megakaryocytes to mature in vitro, and thereby leading to completion of the present invention.

Namely, the present invention relates to that indicated below.

[A1] A highly functional platelet production promoting agent which comprises one or a plurality of aryl hydrocarbon receptor (AhR) antagonists and one or a plurality of Rho-associated coiled-coil forming kinase (ROCK) inhibitors.

[A2] The platelet production promoting agent described in [A1], wherein the AhR antagonist is selected from the group consisting of 4-(2-(2-(benzo[b]thiophen-3-yl)-9-isopropyl-9H-purin-6-ylamino)ethyl)phenol (SR-1), 2-methyl-2H-pyrazole-3-carboxylic acid (2-methyl-4-o-tolylazo-phenyl)-amide (CH-223191), N-[2-(3H-indol-3-yl)ethyl]-9-isopropyl-2-(5-methyl-3-pyridyl)purin-6-amine (GNF-351), 6,2',4'-trimethoxyflavone (TMF) and 3',4'-dimethoxyflavone (DMF).

[A3] The platelet production promoting agent described in [A1] or [A2], wherein the ROCK inhibitor is selected from the group consisting of Y27632, Y39983, fasudil hydrochloride, ripasudil, SLX-2119, RKI-1447, azaindole1, SR-3677, Staurosporine and H1152 dihydrochloride.

[A4] The platelet production promoting agent described in any of [A1] to [A3], wherein the AhR antagonist is SR-1, GNF-351 and/or CH-223191, and the ROCK inhibitor is Y27632, Y39983, fasudil hydrochloride and/or ripasudil.

[A5] A platelet production method, which comprises a step for bringing the platelet production promoting agent described in any of [A1] to [A4] into contact with megakaryocytes or progenitor cells thereof.

[A6] The method described in [A5], wherein the contact step is carried out under conditions of not using feeder cells.

[A7] The method described in [A6], which is carried out under shake culturing conditions.

[A8] The method described in any of [A5] to [A7], further comprising a step for suppressing the expression or function of high mobility group At-hook (HMGA) proteins in the megakaryocytes or progenitor cells thereof.

[A9] The method described in [A8], wherein suppression of the expression or function of the HMGA proteins is carried out by siRNA or miRNA that directly or indirectly suppresses expression of HMGA gene.

[A10] The method described in any of [A5] to [A9], wherein the megakaryocytes are cells obtained by overexpressing at least one gene selected from the group consisting of a cancer gene, polycomb gene and apoptosis suppressor gene in cells less differentiated than the megakaryocytes, followed by terminating the overexpression.

[A11] The method described in [A10], wherein the cells less differentiated than the megakaryocytes are hematopoietic progenitor cells produced from pluripotent stem cells.

[A12] The method described in any of [A5] to [A11], further comprising a step for recovering platelets from the megakaryocytes.

[A13] A platelet preparation containing platelets produced according to the method described in any of [A5] to [A12].

[B1] A platelet production method, comprising a step for culturing megakaryocytes in which the expression or function of HMGA proteins has been suppressed.

[B2] The method described in [B1], wherein the suppression of the expression or function of HMGA proteins is carried out using siRNA against HMGA gene.

[B3] The method described in [B1] or [B2], wherein the culturing step is carried out in the presence of an aryl hydrocarbon receptor (AhR) antagonist.

[B4] The method described in any of [B1] to [B3], wherein the culturing step is carried out in the presence of a ROCK inhibitor.

[B5] The method described in any of [B1] to [B4], wherein the culturing step is carried out under conditions of not using feeder cells.

[B6] The method described in any of [B1] to [B5], further comprising a step for recovering platelets from a culture obtained according to the culturing step.

[B7] A platelet preparation containing platelets produced according to the method described in any of [B1] to [B6].

[B8] A method for maturating megakaryocytes, comprising a step for suppressing the expression or function of HMGA proteins in megakaryocytes.

[B9] The method described in [B8], wherein the step for suppressing the expression or function of HMGA proteins is carried out by siRNA or miRNA that suppresses expression of HMGA gene.

[B10] The method described in [B8], wherein the step for suppressing the expression or function of HMGA proteins is carried out using siRNA or miRNA against HMGA gene.

[B11] The method described in any of [B8] to [B10], wherein the step for suppressing the expression or function of HMGA proteins is carried out by culturing in a medium containing an AhR antagonist.

[B12] The method described in any of [B8] to [B11], wherein the step for suppressing the expression or function of HMGA proteins is carried out by culturing in a medium containing a ROCK inhibitor.

[B13] The method described in any of [B8] to [B12], wherein the step for suppressing the expression or function of HMGA proteins is carried under conditions of not using feeder cells.

[B14] The method described in any of [B3] to [B6] and [B11] to [B13], wherein the AhR antagonist is selected from the group consisting of 4-(2-(2-(benzo[b]thiophen-3-yl)-9-isopropyl-9H-purin-6-ylamino)ethyl)phenol (SR-1), 2-methyl-2H-pyrazole-3-carboxylic acid (2-methyl-4-o-tolylazo-phenyl)-amide (CH-223191), N-[2-(3H-indol-3-yl)ethyl]-9-isopropyl-2-(5-methyl-3-pyridyl)purin-6-amine (GNF-351), 6,2',4'-trimethoxyflavone (TMF) and 3',4'-dimethoxyflavone (DMF).

[B15] The method described in any of [B4] to [B6] and [B12] to [B14], wherein the ROCK inhibitor is selected from the group consisting of Y27632, Y39983, fasudil hydrochloride, ripasudil, SLX-2119, RKI-1447, azaindole1, SR-3677, Staurosporine and H1152 dihydrochloride.

[B16] The method described in any of [B1] to [B15], wherein the megakaryocytes are cells in which at least one gene selected from the group consisting of a cancer gene, polycomb gene and apoptosis suppressor gene has been overexpressed in cells less differentiated than the megakaryocytes followed by terminating that overexpression.

[B17] The method described in [B16], wherein the cells less differentiated than the megakaryocytes are hematopoietic progenitor cells produced from pluripotent stem cells.

[B18] Megakaryocytes in which the expression or function of HMGA proteins has been suppressed.

[B19] The megakaryocytes described in [B18], containing siRNA, miRNA or a nucleic acid encoding the same that suppresses the expression of HMGA proteins.

[B20] The megakaryocytes described in [B18] or [B19], containing at least one exogenous gene selected from the group consisting of a cancer gene, polycomb gene and apoptosis suppressor gene in a chromosome thereof.

[B21] A platelet production method, comprising a step for culturing megakaryocytes in a medium containing an aryl hydrocarbon receptor (AhR) antagonist.

[B22] The method described in [B21], wherein the medium further contains a ROCK inhibitor.

[B23] The method described in [B21] or [B22], wherein the culturing step is carried out under conditions of not using feeder cells.

[B24] The method described in any of [B21] to [B23], wherein the AhR antagonist is selected from the group consisting of 4-(2-(2-(benzo[b]thiophen-3-yl)-9-isopropyl-9H-purin-6-ylamino)ethyl)phenol (SR-1), 2-methyl-2H-pyrazole-3-carboxylic acid (2-methyl-4-o-tolylazo-phenyl)-amide (CH-223191), N-[2-(3H-indol-3-yl)ethyl]-9-isopropyl-2-(5-methyl-3-pyridyl)purin-6-amine (GNF-351), 6,2',4'-trimethoxyflavone (TMF) and 3',4'-dimethoxyflavone (DMF).

[B25] The method described in any of [B21] to [B24], wherein the ROCK inhibitor is selected from the group consisting of Y27632, Y39983, fasudil hydrochloride, ripasudil, SLX-2119, RKI-1447, azaindole1, SR-3677, Staurosporine and H1152 dihydrochloride.

[B26] The method described in any of [B21] to [B25], wherein the megakaryocytes are cells in which at least one gene selected from the group consisting of a cancer gene, polycomb gene and apoptosis suppressor gene has been overexpressed in cells less differentiated than the megakaryocytes followed by terminating that overexpression.

[B27] The method described in [B26], wherein the cells less differentiated than the megakaryocytes are hematopoietic progenitor cells produced from pluripotent stem cells.

Advantageous Effects of Invention

According to the present invention, highly functional platelets can be efficiently produced without using feeder cells. Since the use of feeder cells is not required, an upright, large-scale culturing apparatus can be used to produce platelets, and platelets for clinical use can be efficiently produced in large volume.

BRIEF DESCRIPTION OF THE DRAWINGS

FIG. 3 indicates the results of measuring the number and function of platelets produced by carrying out shake culturing at various concentrations of SR-1 in megakaryocyte medium.

FIG. 4 indicates the results of measuring the number and function of platelets produced by carrying out shake culturing at various seeding densities of megakaryocytes during addition of SR-1.

FIG. 5 indicates the results of measuring the number and function of platelets produced by adding SR-1 analogues to megakaryocyte medium and carrying out static culturing.

FIG. 6B indicates the results of measuring the number and function of platelets produced by adding various concentrations of SR-1 analogues (TMF or DMF) to megakaryocyte medium and carrying out static culturing.

FIG. 15 indicates the results of carrying out flow cytometry on a culture in the case of FIG. 14 using anti-CD62p antibody and anti-PAC-1 antibody.

DESCRIPTION OF EMBODIMENTS (First Aspect)

Figure 1:
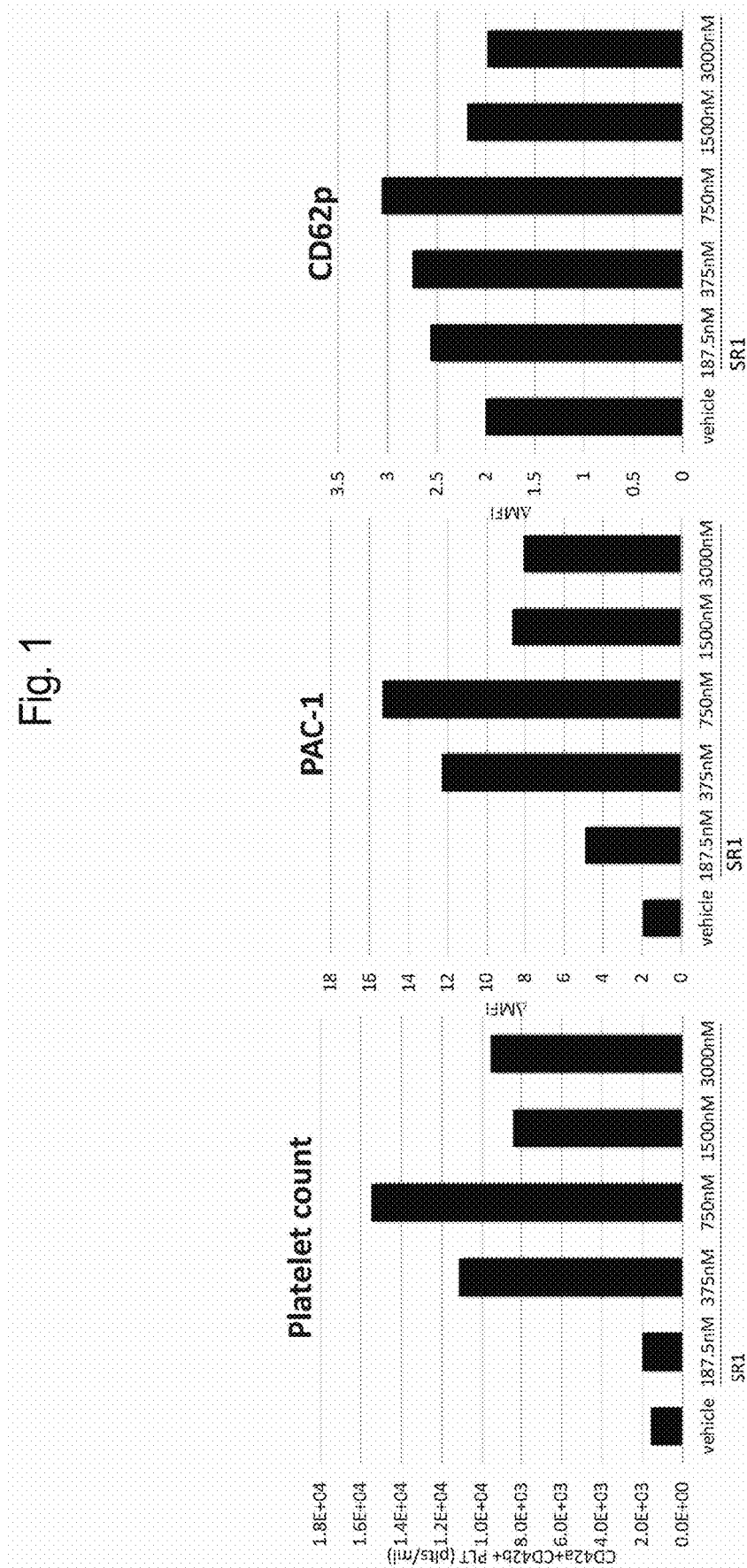
FIG. 1 indicates the results of measuring the number and function of platelets produced by carrying out static culturing at various concentrations of SR-1 (AhR antagonist) in a megakaryocyte medium.

In a first aspect thereof, the present invention provides a platelet production promoting agent containing one or a plurality of aryl hydrocarbon receptor (AhR) antagonists or one or a plurality of ROCK (Rho-associated coiled-coil forming kinase) inhibitors. In another aspect, the present invention further provides a platelet production method that comprises a step for bringing megakaryocytes or progenitor cells thereof into contact with the above-mentioned platelet production promoting agent.

As used herein, "megakaryocytes" refer to the largest cells present in bone marrow in the body, and are characterized by releasing platelets. In addition, megakaryocytes are also characterized by being positive for cell surface markers CD41a, CD42a and CD42b, and may also further express markers selected from the group consisting of CD9, CD61, CD62p, CD42c, CD42d, CD49f, CD51, CD110, CD123, CD131 and CD203c. Although megakaryocytes have a genome that is 16 times to 32 times larger than that of normal cells when they become multinucleated (polyploidy), in the present description, in the case of simply referring to megakaryocytes, both multinucleated megakaryocytes and megakaryocytes prior to multinucleation are included as long as they are provided with the above-mentioned characteristics. "Megakaryocytes prior to multinucleation" have the same meaning as "immature megakaryocytes" or "growth phase megakaryocytes".

Megakaryocytes can be obtained by various known methods. A non-limiting example of a method for producing megakaryocytes is described in WO 2011/034073. In this method, infinitely proliferating immortalized megakaryocytes can be obtained by overexpressing a cancer gene and a polycomb gene in "cells less differentiated than megakaryocytes", or in other words, megakaryocyte progenitor cells (also simply referred to as "progenitor cells" in the subject description). In addition, according to the method described in WO 2012/157586, immortalized megakaryocytes can also be obtained by overexpressing an apoptosis suppressor gene in "cells less differentiated than megakaryocytes". These immortalized megakaryocytes become multinucleated and release platelets as a result of terminating this overexpression of gene.

Methods described in the above-mentioned publications may also be combined to obtain megakaryocytes. In that case, overexpression of a cancer gene, polycomb gene and apoptosis suppressor gene may be carried out simultaneously or sequentially. For example, multinucleated megakaryocytes may be obtained by overexpressing a cancer gene and polycomb gene, suppressing the overexpression thereof, and then overexpressing an apoptosis suppressor gene followed by suppressing the overexpression thereof. In addition, multinucleated megakaryocytes can also be obtained by simultaneously overexpressing a cancer gene, polycomb gene and apoptosis suppressor gene followed by simultaneously suppressing the overexpression thereof. Multinucleated megakaryocytes can also be obtained by first overexpressing a cancer gene and polycomb gene followed by overexpressing an apoptosis suppressor gene, and finally simultaneously suppressing the overexpression thereof.

In the present description, "cells less differentiated than megakaryocytes" or "megakaryocyte progenitor cells" refer to cells having the ability to differentiate into megakaryocytes that are in various stages of differentiation, ranging from hematopoietic stem cells to megakaryocytes. Non-limiting examples of cells less differentiated than megakaryocytes include hematopoietic stem cells, hematopoietic progenitor cells, CD34-positive cells and megakaryocyte-erythroid progenitors (MEP). These cells can be obtained by isolating from, for example, bone marrow, umbilical cord blood or peripheral blood, and can be further obtained by inducing to differentiate from less differentiated cells such as ES cells, iPS cells and other pluripotent stem cells.

In the present description, a "cancer gene" refers to a gene that induces a malignant transformation of cells in the body, and examples thereof include MYC family genes (such as c-MYC, N-MYC or L-MYC), SRC family genes, RAS family genes, RAF family genes, and protein kinase family genes such as c-Kit, PDGFR and Abl.

In the present description, a "polycomb gene" is known to be a gene that functions to avoid cell aging by negatively controlling the CDKN2a (INK4a/ARF) gene (Okura, et al., Regenerative Medicine, Vol. 6, No. 4, pp. 26-32; Jseus, et al., Nature Reviews Molecular Cell Biology, Vol. 7, pp. 667-677, 2006; Proc. Natl. Acad. Sci. USA, Vol. 100, pp. 211-216, 2003). Non-limiting examples of polycomb genes include BMI1, Mel18, Ring1a/b, Phc1/2/3, Cbx2/4/6/7/8, Ezh2, Eed, Suz12, HADC and Dnmt1/3a/3b.

In the present description, an "apoptosis suppressor gene" refers to a gene having a function that suppresses cell apoptosis, and examples thereof include BCL2 gene, BCL-xL gene, Survivin gene and MCL1 gene.

Overexpression of a gene and termination of that overexpression can be carried out by a method described in WO 2011/03473, WO 2012/157586, WO 2014/123242 or Nakamura, S. et al., Cell Stem Cell. 14, 535-548, 2014, as well as other known methods or methods in accordance therewith.

In the present description, an "aryl hydrocarbon receptor (AhR)" refers to a transcription factor belonging to the Per/ARNT/SIM(PAS) family. AhR is inactive when not bound by a ligand, and migrates into the nucleus when bound by an aryl hydrocarbon compound serving as a ligand. Within the nucleus, AhR forms a heterodimer referred to as AhR nuclear translocator (ARNT) and subsequently activates transcription by binding to a xenobiotic response element (XRE) present in DNA.

In the present description, an "AhR antagonist" refers to a substance that suppresses all or a portion of at least one reaction that occurs when an agonist binds to AhR. The AhR antagonist may act directly on AhR or may act indirectly on AhR through the action of another substance.

In the present description, an "AhR agonist" refers to a substance that induces at least one reaction that is induced in the case an intrinsic ligand thereof has bound to AhR. The AhR agonist may act directly on AhR or may act indirectly on AhR through another substance.

A "substance that acts on AhR" includes, but is not limited to, low molecular weight compounds, high molecular weight compounds, proteins such as antibodies or fragments thereof, peptides and nucleic acids.

Non-limiting examples of AhR antagonists used in the present invention include the following:
4-(2-(2-(benzo[b]thiophen-3-yl)-9-isopropyl-9H-purin-6-ylamino)ethyl)phenol (SR-1),
α-naphthoflavone,
1,4-dihydroxyanthraquinone
1,5-dihydroxyanthraquinone,
1,8-dihydroxyanthraquinone,
galangin,
resveratrol,
2-methyl-2H-pyrazole-3-carboxylic acid (2-methyl-4-o-tolylazo-phenyl)-amide (CH-223191),
N-[2-(3H-indol-3-yl)ethyl]-9-isopropyl-2-(5-methyl-3-pyridyl)purin-6-amine (GNF-351),
2-(29-amino-39-methoxyphenyl)-oxanaphthalen-4-one (PD98059),
(Z)-3-[(2,4-dimethylpyrrol-5-yl)methylidenyl]-2-indolinone (TSU-16),
2-(29-amino-39-methoxyphenyl)-oxanaphthalene-4-one (PD98059),
6,2',4'-trimethoxyflavone (TMF), and
3',4'-dimethoxyflavone (DMF).

The AhR is preferably SR-1, GNF-351, CH-223191, TMF or DMF, more preferably SR-1, GNF-351 or CH-223191, and even more preferably GNF-351 or SR-1 from the viewpoints of culturing megakaryocytes under conditions in the absence of feeder cells and increasing the number and/or improving the function of platelets produced. GNF-351 is particularly preferable since it demonstrates effects equal to or better than those of SR-1 and CH-223191 at lower concentrations. A plurality of AhR antagonists can be used in combination provided the desired effects are not impaired.

In addition to the above-mentioned examples, compounds described as AhR antagonists in WO 2012/015914 can also be used in the present invention.

There are no particular limitations on the concentration of AhR antagonist in the step for contacting with megakaryocytes and can be suitably determined by a person with ordinary skill in the art. For example, if the concentration of AhR antagonist in the medium is 200 nM to less than 1000 nM in the case of using SR-1, 0.2 µM to less than 4 µM in the case of using CH-223191, 20 nM to less than 300 nM in the case of using GNF-351, 2.5 µM to less than 40 µM in the case of using TMF, or 2.5 µM to less than 40 µM in the case of using DMF, the number and function of the resulting platelets can be enhanced, although the AhR antagonist may also be present in an amount outside these ranges.

In the case of using "cells in which at least one gene selected from the group consisting of a cancer gene, polycomb gene and apoptosis suppressor gene has been overexpressed in cells less differentiated than megakaryocytes followed by terminating that overexpression", there are no particular limitations on the time of that overexpression and can be suitably determined by a person with ordinary skill in the art.

Furthermore, the cells may be subcultured following overexpression, and although there are no particular limitations on the amount of time from the final round of subculturing to the day on which overexpression is terminated, that amount of time may be, for example, 1 day, 2 days or 3 days or more.

Although there are no particular limitations on the time at which the AhR antagonist is contacted with the megakaryocytes or progenitor cells thereof provided the production volume and/or function of the platelets is enhanced, the megakaryocytes are preferably at least multinucleated and in an early stage of maturation.

In the case of proceeding with multinucleation of immortalized megakaryocytes by producing immortalized megakaryocytes by overexpressing a cancer gene, polycomb gene and apoptosis suppressor gene in cells less differentiated than megakaryocytes followed by terminating that overexpression, it is preferable to add AhR antagonist to the medium after terminating overexpression.

There are no particular limitations on the time period during which the megakaryocytes are contacted with the AhR antagonist. When the AhR antagonist is added to the medium after overexpression has been terminated, functional platelets are gradually released starting on about the third day after adding AhR antagonist to the medium, and the number of platelets increases with the number of days of culturing. In the case of adding SR-1 as AhR antagonist, although highly functional platelets in particular tend to be obtained after culturing for 5 days, the duration of culturing may be shortened or lengthened provided functional platelets are obtained.

There are no particular limitations on the amount of time until AhR antagonist is added to the medium after overexpression of the above-mentioned genes in the megakaryocytes has been terminated, and culturing may be started in the presence of AhR antagonist within 1 day, 2 days or 3 days or more. The AhR antagonist may be added to the medium in one or more additions during the culturing period.

Megakaryocytes are able to contact a ROCK inhibitor in addition to the AhR antagonist. The combined use of an AhR antagonist and ROCK inhibitor makes it possible to significantly enhance the number and function of the platelets produced. In particular, the effect of promoting platelet production demonstrates a synergistic effect in comparison with the case of respectively using the AhR antagonist and ROCK inhibitor alone. In the present description, a "ROCK inhibitor" refers to an antagonist of Rho-associated coiled-coil forming kinase (ROCK). Examples of ROCK inhibitors include, but are not limited to, Y27632, Y39983, fasudil hydrochloride, ripasudil, SLX-2119, RKI-1447, azaindole1, SR-3677, Staurosporine and H1152 dihydrochloride, AR-12286 and INS-117548. A plurality of ROCK inhibitors can be used in combination provided the desired effects are not impaired.

The ROCK inhibitor is preferably Y27632, Y39983, fasudil hydrochloride or ripasudil and more preferably Y39983 from the viewpoints of culturing megakaryocytes under conditions in the absence of feeder cells and increasing the number and/or improving the function of the platelets produced. Although there are no particular limitations on the time at which the ROCK inhibitor is contacted with the megakaryocytes or progenitor cells thereof provided the production volume and/or function of the platelets is enhanced, the megakaryocytes are preferably those which are at least multinucleated.

As indicated in the examples to be subsequently described, when megakaryocytes or progenitor cells thereof are contacted with an AhR antagonist and ROCK inhibitor, the number of the resulting platelets produced is increased and the function thereof is improved even under conditions of culturing in the absence of feeder cells. What is particularly noteworthy is that, in comparison with the case of using each of AhR antagonist and ROCK inhibitor alone, the combined use of the two drugs acts synergistically on the effect of promoting platelet production. Although there are no particular limitations on the combination of AhR antagonist and ROCK inhibitor, a combination of one or a plurality of AhR antagonists selected from the group consisting of SR-1, GNF-351 and CH-223191, and one or a plurality of ROCK inhibitors selected from the group consisting of Y27632, Y39983, fasudil hydrochloride and ripasudil, is preferable from the viewpoint of significantly enhancing the number and function of platelets. Among these, the combination of SR-1 and/or GNF-351 and Y27632 and/or Y39983 is more preferable. In the case of using the combination of GNF-351 and Y39983 in particular, the production volume of functional platelets increases significantly (data not shown). The AhR antagonist and ROCK inhibitor may be added simultaneously or either drug may be added first.

"Platelets" constitute a portion of the cellular components of blood, and in the present description, are characterized by being CD41a-positive and CD42b-positive. In addition to fulfilling an important role in thrombus formation and hemostasis, platelets are also involved in tissue regeneration following injury and the pathophysiology of inflammation. When platelets are activated by such factors as hemorrhaging, receptors of cell adhesive factors such as integrin αIIBβ3 (glycoprotein IIb/IIIa; complex of CD41a and CD61) are expressed on the membrane thereof. As a result, the platelets begin to aggregate, thrombi are formed due to the clotting of fibrin by various types of blood coagulation factors released from the platelets, and hemostasis progresses.

When used in the present description, the "functions" of platelets refer to those functions known in the art such as a circulation function, thrombus formation function or hemostasis function. In the present description, the expressions of "highly functional", "high platelet function" or "activated", or expressions similar thereto, refer to platelet function (or physiological activity), as measured by at least one method to be subsequently described, being equal to or higher, and preferably significantly higher, or shaped platelets being equal to or lower, and preferably significantly lower, in comparison with platelets obtained by a conventional method not using an AhR antagonist or ROCK inhibitor, or platelets isolated from the body. Alternatively, these expressions refer to a state in which a person with ordinary skill in the art is able to judge that platelet function has tended to be improved even if the difference is not significant.

Alternatively, in the present invention, expressions such as "highly functional platelets", "high platelet function" or "activated" mean that platelet function, as measured by at least one method to be subsequently described, is 50% or more, 60% or more, 70% or more, 80% or more or 90% or more of that of platelets obtained by a conventional method not using an AhR antagonist or ROCK inhibitor, or natural platelets isolated from the body.

The above-mentioned platelet function can be evaluated by measuring according to a known method. For example, the amount of activated platelets can be measured using PAC-1 antibody, which is an antibody that specifically binds to the activation marker, integrin αIIBβ3 (glycoprotein IIb/IIIa; complex of CD41a and CD61), present on the membrane of activated platelets. In addition, the amount of activated platelets may also be similarly measured by detecting the platelet activation marker, CD62b (P-selectin), with antibody. Measurement of the amount of platelets can be carried out by, for example, gating the platelets with antibody to activation-independent platelet marker CD61 or CD41 using flow cytometry, followed by detecting binding of PAC-1 antibody or anti-CD62P antibody to the platelets. These steps may also be carried out in the presence of adenosine diphosphate (ADP).

Figure 6A:
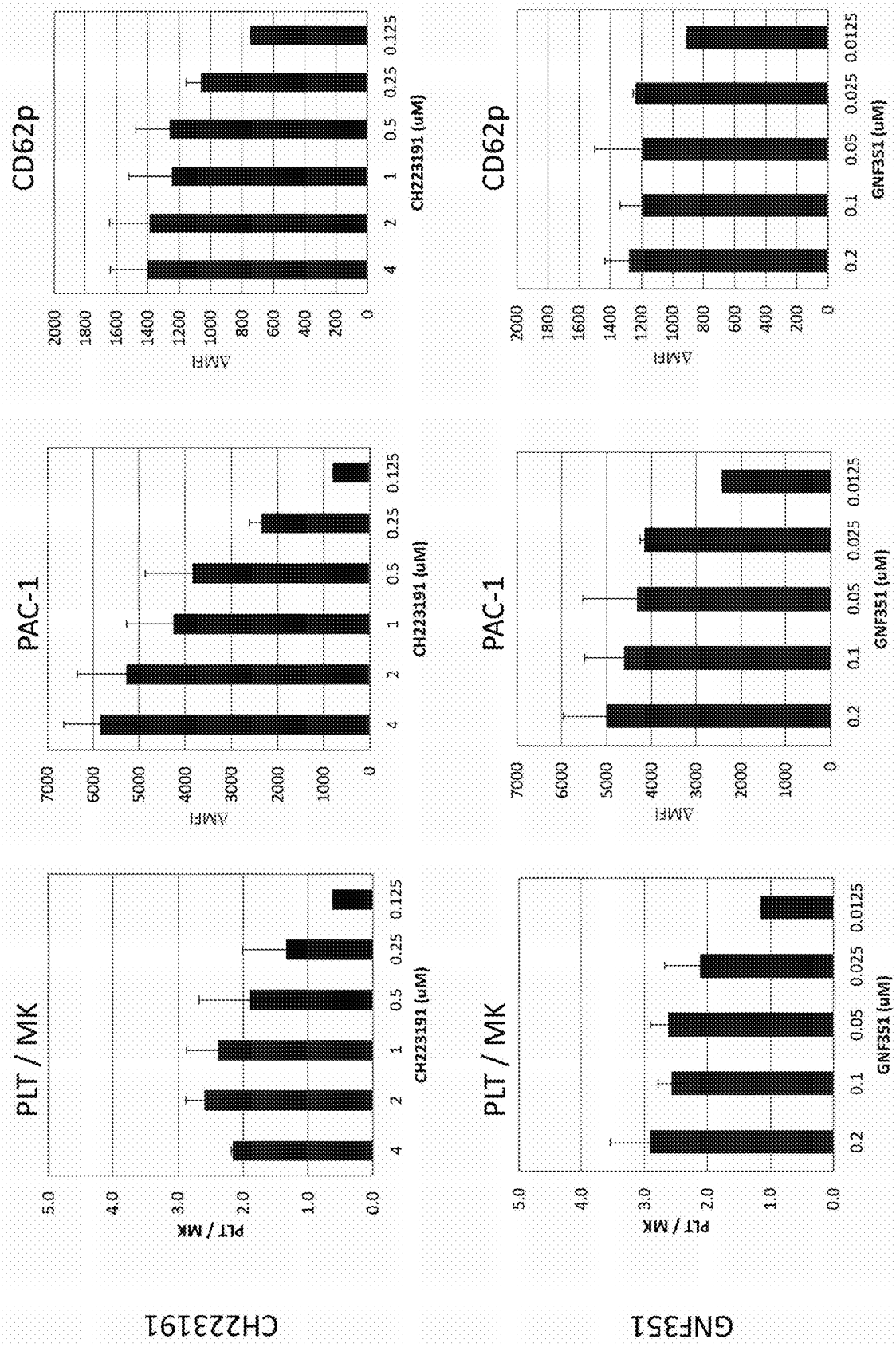
FIG. 6A indicates the results of measuring the number and function of platelets produced by adding various concentrations of SR-1 analogues (CH-223191 or GNF-351) to megakaryocyte medium and carrying out static culturing.

In addition, evaluation of platelet function can be carried out by observing whether or not the platelets bind with fibrinogen in the presence of ADP. The activation of integrin, which is initially required for thrombus formation, occurs as a result of platelets binding with fibrinogen. Moreover, evaluation of platelet function can also be carried out by a method comprising visualizing and subsequently observing the ability to form thrombus in vivo as indicated in FIG. 6 of WO 2011/034073.

Evaluation of the circulation function of platelets in the body can be carried out in accordance with ordinary methods. More specifically, after administering platelets at $2 \times 10^8$ platelets/animal into the tail veins of NOG mice serving as a thrombocytopenia model induced by gamma radiation (2.4 Gy), human-derived platelets present in blood collected from the jugular vein at fixed intervals are assayed using anti-human CD41 antibody to evaluate the circulation function of the platelets.

Evaluation of the hemostasis function of platelets can be evaluated in accordance with ordinary methods. More specifically, after administering platelets at $2 \times 10^8$ platelets/animal into the tail veins of NOG mice serving as a thrombocytopenia model induced by gamma radiation (2.4 Gy), the tail vein is punctured (2 cm from the tip) using a 28G syringe under anesthesia (urethane, 1.5 g/kg) followed by measuring the amount of time until hemostasis occurs while immersing the tip of the tail in PBS warmed to 37° C. to evaluate hemostasis function.

On the other hand, platelets are evaluated as having undergone degradation or being abnormal in the case the expression rate of CD42b by the platelets is low or in the case the annexin V positive rate is high. These platelets are not useful clinically since they do not have adequate ability to form thrombi or demonstrate hemostasis.

In the present description, "platelet degradation" refers to a reduction in CD42b (GPIbα) on the platelet surface. Thus, degraded platelets include platelets for which expression of CD42b has decreased and platelets in which the extracellular region of CD42b has been cleaved by a shedding reaction. When CD42b is no longer present on the platelet surface, conjugation with von Willebrand factor (VWF) is no longer possible, and as a result thereof, platelets lose the function of coagulating blood. Platelet degradation can be evaluated by using as an indicator the ratio of the CD42b negative rate (or number of CD42b-negative particles) to the CD42b positive rate (or number of CD42b-positive particles) present in a platelet fraction. Platelets proceed to degrade as the ratio of the CD42b negative rate to the CD42b positive rate becomes higher, or as the number of CD42b-negative particles becomes large relative to the number of CD42b-positive particles. The CD42b positive rate refers to the ratio of platelets contained in a platelet fraction that are capable of being bound by anti-CD42b antibody, while the CD42b negative rate refers to the ratio of platelets not bound by anti-CD42b antibody.

In the present description, "abnormal platelets" refer to platelets in which a negatively charged phospholipid in the form of phosphatidylserine has become exposed from the inside to the outside of the lipid bilayer. In the body, phosphatidylserine is exposed on the surface accompanying platelet activation, and the blood coagulation cascade reaction is known to be amplified as a result of numerous blood clotting factors binding thereto. On the other hand, in abnormal platelets, a large amount of phosphatidylserine is present on the surface at all times, and when such platelets are administered to a patient, an excessive blood clotting reaction is induced that has the potential for leading to a serious condition such as disseminated intravascular coagulation syndrome. Since annexin V binds to phosphatidylserine, phosphatidylserine on the surface of platelets can be detected by flow cytometry using the amount of fluorescent-labeled annexin V bound as an indicator. Accordingly, the amount of abnormal platelets can be evaluated based on the annexin V positive rate, or in other words, the ratio or number of platelets bound by annexin. The number of abnormal platelets becomes higher the higher the annexin V positive rate, or the larger the number of annexin V particles.

In addition, evaluation of platelet function can also be carried out by observing whether or not the platelets bind to fibrinogen in the presence of ADP. Integrin, which is required for initial thrombus formation, is activated as a result of platelets binding to fibrinogen.

Moreover, evaluation of platelets can also be carried out by a method comprising visualizing and subsequently observing the ability to form thrombus in vivo as indicated in FIG. 6 of WO 2011/034073.

In the case of proceeding with multinucleation of immortalized megakaryocytes by producing immortalized megakaryocytes by overexpressing a cancer gene, polycomb gene and apoptosis suppressor gene in cells less differentiated than megakaryocytes followed by terminating that overexpression, it is preferable to add ROCK inhibitor to the medium after terminating overexpression.

(Second Aspect)

In a second aspect thereof, the present invention provides a method for producing platelets that comprise a step for suppressing the expression or function of a high-mobility group At-hook (HMGA) protein in megakaryocytes or progenitor cells thereof.

High-mobility group At-hook (or high-mobility group A) (HMGA) protein is a non-histone chromatin protein that mainly binds to DNA containing large amounts of AT, and is known as HMGA1 and HMGA2. HMGA as used herein particularly, is preferably HMGA2. Human HMGA2 protein is also referred to as NCBI reference sequence: NP_001287847.1.

In the present description, the term "protein expression" is used based on the concept of including both transcription and translation, and in the case of referring to as "suppressing expression", refers suppressing all or a portion of expression at the transcription level or translation level.

The step for suppressing the expression or function of HMGA protein can be carried out using a known method or a method in accordance therewith.

In addition, the dominant negative method may be used as a method for suppressing the function of HMGA protein. The dominant negative method comprises expressing a large amount of HMGA protein, for which the activity thereof has been lowered or lost by the introduction of a mutation, into cells to overwhelmingly increase the ratio of inactive HMGA protein to normal HMGA protein in the cells and obtain cells that exhibit behavior that prevents the function of HMGA protein from being obtained.

Anti-HMGA antibody may be used to inhibit the function of HMGA protein. Antibody produced according to a known method or commercially available antibody can be used for the anti-HMGA antibody, and any such antibody may be used provided the effects of the present invention are obtained through the suppression of the function of HMGA proteins.

An example of a method for suppressing expression of HMGA proteins includes using miRNA that directly or indirectly suppresses expression of HMGA gene. The miRNA may be that which acts directly on HMGA gene or that which acts indirectly. For example, this method can be carried out by using miRNA referred to as let-7. In the present invention, although let-7 is any one miRNA selected from the group consisting of hsa-let-7a-1, hsa-let-7a-2, hsa-let-7a-3, hsa-let-7b, hsa-let-7c, hsa-let-7d, hsa-let-7e, hsa-let-7f-1, hsa-let-7f-2, hsa-let-7g and hsa-let-7i in the case of humans, for example, let-7 of other animal species can also be used. The sequence of let-7 and so forth can be suitably obtained from information registered in a database (such as http://www.mirbase.org/ or http://www.micror-na.org/). In the present invention, let-7 is preferably hsa-let-7b.

In addition, suppression of the expression of HMGA2 proteins can also be carried out using a method comprising using miRNA that suppresses the expression of Lin28b, which negatively controls the expression of let-7. An example of this miRNA is miR181a. Although miR181a is any one miRNA selected from the group consisting of hsa-mir-213, hsa-mir-181a-1 and hsa-mir-181a-2 in the case of humans, for example, miR181a from other animal species can also be used. The sequence of miR181a and so forth can be suitably obtained from information registered in the same databases as described above.

"miRNA" refers to non-coding RNA having a short chain (of 20 to 25 bases) present in cells that is involved in regulating gene expression through inhibition of translation from mRNA to proteins and decomposition of mRNA. This miRNA functions by being transcribed as pri-miRNA, differing by a single strand therefrom, that is capable of adopting a hairpin loop structure containing miRNA and a complementary strand thereof, and having a portion thereof cleaved by an enzyme referred to as DROSHA within the nucleus of the cell resulting in the formation of pre-miRNA, followed by this pre-miRNA being transported outside the cell and further cleaved by Dicer. Thus, in the present invention, the let-7 or miR181 used may be single-stranded pri-miRNA or double-stranded pre-miRNA.

Examples of methods that may be used to suppress expression of HMGA gene include the antisense method, the ribozymes method and the RNAi method.

The antisense method comprises suppressing expression of a gene using a single-stranded nucleic acid typically 10 to 100 bases in length, and preferably 15 to 30 bases in length, that has a base sequence complementary to the target gene (basically, the transcription product thereof in the form of mRNA). Gene expression is suppressed by introducing the antisense nucleic acid into cells and hybridizing the antisense nucleic acid with the target gene. The antisense nucleic acid is not required to be completely complementary to the target gene provided it allows the effect of suppressing expression of the target gene to be obtained. The antisense nucleic acid can be suitably designed by a person with ordinary skill in the art using known software and the like. The antisense nucleic acid may be any of DNA, RNA or DNA/RNA chimera, and is not required to be modified.

Ribozymes are nucleic acid molecules that catalytically hydrolyze a target RNA, and are composed of an antisense strand having a sequence complementary to the target RNA and a catalyst core region responsible for the cleaving reaction. Ribozymes can be suitably designed by a person with ordinary skill in the art in accordance with known methods. Although ribozymes are typically RNA molecules, DNA-RNA chimera molecules can also be used.

The RNAi method is a sequence-specific gene expression suppression mechanism induced by a double-stranded nucleic acid. In addition to target specificity being extremely high, it also offers a high degree of safety since it uses the gene expression suppression mechanism inherently present in the body.

An example of a double-stranded nucleic acid having an RNAi effect is siRNA. In the case of using in mammals, siRNA is double-stranded RNA normally having about 19 to 30 bases and preferably 21 to 25 bases. Typically, one of the strands of double-stranded nucleic acids demonstrating an RNAi effect has a base sequence complementary to a portion of a target nucleic acid, while the other strand has a sequence complementary thereto. siRNA suppressing the expression of HMGA can be suitably designed by a person with ordinary skill in the art using known software and the like, and the target sequence used in the examples to be subsequently described is exemplified as one of strands a double-stranded nucleic acid sequence. siRNA suppressing the expression of HMGA may act directly on the HMGA gene (by containing a sequence that is complementary to a portion of the HMGA gene) or may act indirectly (by suppressing the expression of a gene other than HMGA gene to suppress expression of HMGA gene as a result thereof).

The above-mentioned let-7, miR181a, antisense nucleic acid and ribozymes can be expressed within cells by introducing a vector (such as a lentivirus vector) containing nucleic acid respectively encoding the same into the cells, or can be introduced into cells in the form of RNA. In the case of introducing in the form of RNA, the let-7, miR181a, antisense nucleic acid or ribozymes may be introduced into cells by a known method such as lipofection or microinjection, and RNA incorporating 5-methylcytidine and pseudouridine (TriLink Biotechnologies) (Warren, L., Cell Stem Cell, 7: 618-630 (2010)) or DNA-RNA chimera incorporating DNA may also be used to suppress RNA degradation. In the case of uridine or cytidine, the locations of the modified bases can independently be all or a portion of the locations, and in the case of only a portion of the locations, can be random locations at an arbitrary ratio. A vector containing DNA encoding each double strand may be used for the vector containing nucleic acid encoding let-7, miR181a or siRNA, or a vector may be used that contains DNA encoding a single-stranded nucleic acid capable of linking double-stranded nucleic acid through a loop. In the case of siRNA, single-stranded RNA obtained by intracellular transcription may be designed so as to hybridize with a complementary portion of the siRNA within a molecule thereof to adopt a hairpin structure. This type of RNA is referred to as short hairpin RNA (shRNA). When shRNA migrates into the cytoplasm, the loop portion is cleaved by an enzyme (Dicer) resulting in the formation of siRNA and enabling the RNAi effect thereof to be demonstrated.

In the present description, when referring to suppression of the expression of a protein as being "carried out by siRNA" or being "carried out by miRNA", this ultimately means that the siRNA or miRNA suppresses expression, and siRNA, shRNA or miRNA may be administered in the form of RNA, or a vector may be administered that contains nucleic acid encoding siRNA, shRNA or miRNA.

In the case of introducing let-7, miR181a or siRNA or shRNA against HMGA with a vector and the like, expression of that RNA may be controlled by a drug-responsive promoter. A vector capable of drug-responsively controlling RNA in this manner can be acquired from, for example, Takara Bio Inc. In this case, introducing this RNA means that RNA is expressed within cells by contacting with the corresponding drug.

As will be understood from the examples, from the viewpoint of being effective in the megakaryocyte maturation process including multinucleation and enlargement, suppression of the expression or function of HMGA protein may be carried out on megakaryocytes prior to multinucleation, or from the viewpoint of causing multinucleated megakaryocytes to undergo further multinucleation, suppression of the expression or function of HMGA protein may be carried out on multinucleated megakaryocytes. Since multinucleation and enlargement of megakaryocytes are promoted and the number of platelets produced per cell increases dramatically, it is preferable to carry out suppression of the expression or function of HMGA protein in a step for producing platelets from megakaryocytes.

Mature megakaryocytes obtained according to the present invention are able to efficiently produce functional platelets. In the present description, megakaryocyte maturation refers to megakaryocytes becoming sufficiently multinucleated to be able to produce functional platelets. Megakaryocyte maturation can be confirmed by increases in the expression of a group of megakaryocyte maturation-associated genes such as GATA1, p45 NF-E2 or beta1-tubulin, the formation of proplatelets, and intracellular multinucleation.

Furthermore, in the case of proceeding with multinucleation of immortalized megakaryocytes by overexpressing a cancer gene, polycomb gene and apoptosis suppressor gene in cells less differentiated than megakaryocytes to produce immortalized megakaryocytes followed by terminating that overexpression, although there are no particular limitations on whether the above-mentioned suppression of the expression or function of HMGA protein is started before or after termination of the overexpression of those genes, the expression or function of HMGA protein is preferably suppressed at least after having terminated overexpression. Since the number of CD41a-positive cells, namely the number of megakaryocytes prior to multinucleation, tends to decrease by suppressing the expression or function of HMGA protein prior to termination of the overexpression of those genes, the start of suppression of the expression or function of HMGA protein is more preferably carried out after having terminated overexpression of those genes from the viewpoint of maintaining the number of megakaryocytes prior to multinucleation.

(Third Aspect)

In a third aspect thereof, the present invention provides a method for producing megakaryocytes that comprises a step for culturing megakaryocytes, in which the expression or function of HMGA proteins has been suppressed, in the presence of an AhR antagonist and/or ROCK inhibitor. In addition, the culturing step can be carried out in the same manner as the above-mentioned contact step. In another aspect, the method for producing megakaryocytes according to the present invention may also comprise a step for producing platelets.

(Culturing Conditions and Other Parameters)

In any aspect of the present invention, megakaryocyte culturing conditions can include those used during ordinary culturing. For example, the temperature can be a temperature of about 35° C. to about 42° C., about 36° C. to about 40° C. or about 37° C. to about 39° C., and culturing may be carried out in the presence of 5% $CO_2$ and/or 20% $O_2$. Culturing may be carried out by static culturing or shake culturing. According to the present invention, since culturing can be realized under conditions in the absence of feeder cells in the case of using an AhR antagonist such as SR-1, shake culturing is preferable in the case of producing a large number of platelets. There are no particular limitations on the shaking speed in the case of shake culturing, and a shaking speed of, for example, 10 rpm to 200 rpm or 30 rpm to 150 rpm can be used.

In the present invention, megakaryocytes are allowed to mature and platelets are produced from the cytoplasm thereof by culturing the megakaryocytes in the manner described above. Here, maturation of megakaryocytes refers to enabling the megakaryocytes to become multinucleated and release platelets.

There are no particular limitations on the medium used when culturing megakaryocytes, and known media or media in accordance therewith that is preferable for producing platelets from megakaryocytes can be suitably used. For example, media used to culture animal cells can be prepared for use as basal media. Examples of basal media include IMDM medium, Medium 199, Eagle's minimum essential medium (EMEM), αMEM, Dulbecco's modified Eagle's medium (DMEM), Ham's F12 medium, RPMI 1640 medium, Fisher's medium, Neurobasal medium (Life Technologies Corporation) and mixed media thereof.

The medium may contain serum or plasma or may be serum-free. The medium can contain one or more substances such as albumin, insulin, transferrin, selenium, fatty acids, trace elements, 2-mercaptoethanol, thiolglycerol, monothioglycerol (MTG), lipid, amino acids (such as L-glutamine), ascorbic acid, heparin, non-essential amino acids, vitamins, growth factors, low molecular weight compounds, antibiotics, antioxidants, pyruvic acid, buffers, inorganic salts or cytokines as necessary. Cytokines are proteins that promote hematopoietic differentiation, and examples thereof include vascular endothelial growth factor (VEGF), thrombopoietin (TPO), various types of TPO-like agents, stem cell factor (SCF), insulin-transferrin-selenite (ITS) supplement and ADAM inhibitors. IMDM medium containing serum, insulin, transferrin, selenium, thioglycerol, ascorbic acid and TPO is used preferably in the present invention. This IMDM medium may further contain SCF and may further contain heparin. There are no particular limitations on the concentration of each substance, and for example, the concentration of TPO can be about 10 ng/mL to about 200 ng/mL or about 50 ng/mL to about 100 ng/mL, the concentration of SCF can be about 10 ng/m L to about 200 ng/m L or about 50 ng/mL, and the concentration of heparin can be about 10 U/mL to about 100 U/mL or about 25 U/mL. A phorbol ester (such as phorbol 12-myristate-13-acetate (PMA)) may also be added.

Human serum is preferable in the case of using serum. In addition, human plasma and the like may be used in place of serum. According to the method of the present invention, platelets equivalent to those obtained when using serum can be obtained even if these components are used.

In the case of using a drug-responsive gene expression induction system in the manner of a Tet-on® or Tet-off® system for overexpression of a gene or the termination thereof, the corresponding drug such as tetracycline or doxycycline in the overexpression step is contained in the medium, and overexpression may be suppressed by removing the drug from the medium.

The step for culturing megakaryocytes in the present invention can be carried out in the absence of feeder cells. As is indicated in the examples to be subsequently described, according to the method of the present invention, functional platelets can be obtained even if culturing is carried out in the absence of feeder cells.

In the present description, "feeder cells" refer to cells cultured with cells desired to be proliferated or differentiated (target cells) for the purpose of providing an environment required for culturing the target cells. Feeder cells include cells derived from the same species and cells derived from a different species provided they are cells that can be distinguished from the target cells. The feeder cells may be cells that have been treated with an antibiotic or gamma rays so as not to proliferate, or may be cells not subjected to such treatment.

The present invention also includes platelets produced according to the method of the present invention. As indicated in the examples to be subsequently described, platelets produced according to the method of the present invention demonstrate more advanced development of the open canalicular system in comparison with platelets produced in vitro in accordance with conventional methods, and are observed to be morphologically similar to natural platelets from the viewpoint of being able to confirm the presence of mitochondria.

The method for producing a platelet preparation according to the present invention comprises a step for producing platelets in mature megakaryocytes prepared in the manner previously described, and optionally comprises a step for recovering a platelet-rich fraction from the culture and a step for removing blood cell components other than platelets from the platelet fraction. The step for removing blood cell components can be carried out by removing blood cell components other than platelets, including megakaryocytes, using a leukocyte removal filter (such as that manufactured by Terumo Corporation or Asahi Kasei Medical Co., Ltd.). A specific example of a method for producing a platelet preparation is described in WO 2011/034073.

The method for producing a blood preparation according to the present invention comprises a step for producing the above-mentioned platelet preparation and a step for mixing the platelet preparation with other components. An example of the other components is erythrocytes.

Other components contributing to stabilization of the cells may also be added to the platelet preparation and blood preparation.

In addition, the present invention also includes a composition containing multinucleated megakaryocytes, AhR antagonist and medium. The present composition allows the obtaining of highly functional platelets by culturing as is or can be freeze-dried. In the case of freeze-drying in particular, the composition may contain DMSO, glycerol or a commercially available cell cryopreservation reagent that protects cells during freezing. Highly functional platelets can be obtained by thawing and culturing the frozen composition.

Disclosures of all patent documents and non-patent documents cited in the present description are incorporated in the present description in their entirety by reference.

Example 1

Although the following provides a detailed explanation of the present invention based on examples thereof, the present invention is not limited thereto. A person with ordinary skill in the art is able to modify the present invention in various ways without deviating from the significance of the present invention, and such modifications are included within the scope of the present invention.

1. Preparation of Immortalized Megakaryocytes
1-1. Preparation of Hematopoietic Progenitor Cells from iPS Cells Human iPS cells (TKDN SeV2: human fetal skin fibroblast-derived iPS cells established using Sendai virus) were cultured to differentiate into blood cells according to the method described in Takayama, N., et al., J. Exp. Med., 2817-2830 (2010). Namely, human ES/iPS cell colonies were co-cultured for 14 days with C3H10T1/2 feeder cells in the presence of VEGF (R&D Systems, Inc.) at 20 ng/mL to prepare hematopoietic progenitor cells (HPC). Culturing was carried out under culturing conditions of 20% $O_2$ and 5% $CO_2$ (to apply similarly hereinafter unless specifically indicated otherwise).

1-2. Viral Infection of c-MYC and BMI1 into Hematopoietic Progenitor Cells

HPC obtained in the manner previously described were disseminated at $5 \times 10^4$ cells/well in a 6-well plate preliminarily disseminated on C3H10T1/2 feeder cells followed by overexpressing c-MYC and BMI1 using the lentivirus method. At this time, 6 wells were used for each cell line. Namely, virus particles were respectively added to the medium at an MOI ratio of 20, and the cells were infected by spin infection (by centrifugation at 32° C. and 900 rpm for 60 minutes). This procedure was carried out twice at a 12-hour interval. At this time, medium obtained by further adding protamine to a final concentration of 10 μg/mL to medium containing 50 ng/mL of human thrombopoietin (TPO) (R&D Systems, Inc.), 50 ng/mL of human stem cell factor (SCF) (R&D Systems, Inc.) and 2 μg/mL of doxycycline (Dox) in a basal medium (IMDM (Iscove's modified Dulbecco's medium) (Sigma-Aldrich Company Ltd.) containing 15% fetal bovine serum (Gibco Corporation), 1% penicillin-streptomycin-glutamine (Gibco Corporation), 1% insulin, transferrin and selenium solution (ITS-G) (Gibco Corporation), 0.45 mM 1-thioglycerol (Sigma-Aldrich Company Ltd.) and 50 μg/mL L-ascorbic acid (Sigma-Aldrich Company Ltd.)) (to be referred to as differentiation medium) was used for the medium. Furthermore, the lentivirus vector was a tetracycline-regulated inducible vector produced by recombining the mOKS cassette of LV-TRE-mOKS-Ubc-tTA-I2G (Kobayashi, T., et al., Cell, 142, 787-799 (2010)) in c-MYC, BMI1 and BCL-xL (respectively referred to as LV-TRE-c-Myc-Ubc-tTA-I2G, LV-TRE-BMI1-Ubc-tTA-I2G and LV-TRE-BCL-xL-Ubc-tTA-I2G). The virus particles used for infection were prepared by expressing the above-mentioned lentivirus vector in 293T cells.

1-3. Preparation and Maintenance Culturing of Self-Renewing Megakaryocyte Lines

After designating the day on which viral infection with cMYC and BMI1 was carried out according to the above-mentioned method as infection day 0, self-renewing megakaryocyte lines were respectively prepared by culturing the megakaryocytes cells introduced with cMYC and BMI1 as described below.

Infection Day 2 to Infection Day 11

The virus-infected blood cells obtained according to the method described above were recovered by pipetting, and after removing the supernatant by centrifugation for 5 minutes at 1200 rpm, the cells were suspended in fresh differentiation medium and disseminated on fresh C3H10T1/2 feeder cells (6-well plate). Subculturing was carried out by performing the same procedure on day 9 of infection. After counting the number of cells, the cells were disseminated on C3H10T1/2 feeder cells at $1 \times 10^5$ cells/2 mL/well (6-well plate).

Infection Day 12 to Infection Day 13

The same procedure as that performed on infection day 2 was carried out. After counting the number of cells, the cells were disseminated on C3H10T1/2 feeder cells at $3 \times 10^5$ cells/10 mL/100 mm dish (100 mm dish).

Infection Day 14

The blood cells in which viral infection had been completed were recovered and subjected to antibody reactions using 2 μL, 1 μL and 14 of anti-human CD41a-APC antibody (BioLegend Inc.), anti-human CD42b-PE antibody (eBioscience, Inc.) and anti-human CD235ab-Pacific Blue antibody (BioLegend Inc.), respectively, per $1.0 \times 10^5$ cells. Following the reactions, the cells were analyzed using FACS Verse (Becton Dickinson and Company). Those cells having a CD41a positive rate of 50% or higher on day 14 of infection were considered to constitute a self-renewing megakaryocyte line.

1-4. Viral Infection of BCL-xL into Self-Propagating Megakaryocyte Lines

BCL-xL gene was introduced into the above-mentioned self-renewing megakaryocyte lines on day 14 of infection using the lentivirus method. Virus particles were added to the medium to an MOI ratio of 10 followed by infection by spin infection (by centrifugation at 32° C. and 900 rpm for 60 minutes).

1-5. Preparation and Maintenance Culturing of Immortalized Megakaryocyte Lines

Infection Day 14 to Infection Day 18

The self-renewing megakaryocyte lines introduced with BCL-xL gene obtained in the manner described above were recovered and centrifuged for 5 minutes at 1200 rpm. Following centrifugation, the deposited cells were suspended in fresh differentiation medium followed by disseminating on fresh C3H10T1/2 feeder cells at $2 \times 10^5$ cells/2 mL/well (6-well plate).

Infection Day 18: Subculturing

After counting the number of cells, the cells were disseminated at $3 \times 10^5$ cells/10 mL/100 mm dish.

Infection Day 24: Subculturing

After counting the number of cells, the cells were disseminated at $1 \times 10^5$ cells/10 mL/100 mm dish. Maintenance culturing was subsequently carried out by subculturing every 4 to 7 days.

Self-renewing megakaryocyte lines introduced with BCL-xL gene were recovered on day 24 of infection, and after immunostaining using 2 μL, 14 and 14 of anti-human CD41a-APC antibody (BioLegend Inc.), anti-human CD42b-PE antibody (eBioscience, Inc.) and anti-human CD235ab-Pacific Blue (anti-CD235ab-PB) antibody (BioLegend Inc.), respectively, per $1.0 \times 10^5$ cells, the cells were analyzed using FACS Verse (Becton Dickinson and Company), and those cells having a CD41a positive rate of 50% or higher on day 24 of infection were considered to constitute an immortalized megakaryocyte line.

As a result of maintenance culturing of the above-mentioned self-renewing megakaryocyte lines introduced with BCL-xL gene, cells derived from iPS cells (692D2, 1108A2) were able to proliferate for 24 days or more after infection. These cells were considered to constitute an immortalized megakaryocyte line (SeV2-MKCL).

The resulting SeV2-MKCL cells were static cultured in a 10 cm dish (10 mL/dish). The medium was obtained by adding the following components to IMDM serving as the basal medium (concentrations indicate final concentrations).

FBS (#172012, Lot No. 12E261 (Sigma)): 15%
L-glutamine (#25030-081 (Gibco Corporation)): 2 mM
ITS (#41400-045 (Gibco Corporation)): 100-fold dilution
MTG (monothioglycerol, #6145-25ML (Sigma)): 450 μM
Ascorbic acid (#A4544 (Sigma)): 50 μg/mL
Puromycin (#P8833-100MG (Sigma)): 2 μg/mL
SCF (#193-15513 (Wako Pure Chemical Industries, Ltd.)): 50 ng/mL
TOP-like agent: 200 ng/mL Culturing was implemented under conditions of 37° C. and 5% $CO_2$.

Overexpression of BMI1 gene, c-MYC gene and BCL-xL gene was carried out by adding 1 μg/mL of doxycycline (#631311 (Clontech Laboratories, Inc.)) to the medium.

2. Examination of SR-1 Concentration

The immortalized megakaryocyte line (SeV2-MKCL) obtained according to the method described in section 1 was washed twice with PBS(−) and then cultured in medium not containing doxycycline to terminate overexpression. Culturing was implemented by disseminating the cells at 2 mL/well in a 6-well plate at a seeding concentration of $1 \times 10^5$ cells/mL followed by static culturing in the medium indicated below.

The medium was obtained by adding the following components to IMDM serving as the basal medium (concentrations indicate final concentrations).

FBS: 15%
L-glutamine (#25030-081 (Gibco Corporation)): 2 mM
ITS (#41400-045 (Gibco Corporation)): 100-fold dilution
MTG (monothioglycerol, #M6145-25ML (Sigma)): 450 μM
Ascorbic acid (#A4544 (Sigma)): 50 μg/mL
SCF (#193-15513 (Wako Pure Chemical Industries, Ltd.)): 50 μg/mL
TPO-like agent: 200 ng/mL
ADAM inhibitor: 15 μM Culturing was implemented under conditions of 37° C. and 5% $CO_2$.

After simultaneously adding SR-1 at the concentrations shown in FIG. 1 and culturing for 7 days, the number and function of the platelets were measured. The measurement method was as shown below.

The culture supernatant was gently suspended using a 1 mL Pipetman 7 days after culturing to terminate gene expression. 200 μL of the culture broth were dispensed into a 5 mL sample tube followed by staining with the antibodies indicated below.

0.5 μL of PB-labeled anti-CD42a antibody (#48-0428-42 (eBioscience, Inc.))

0.5 μL of PE-labeled anti-CD42b antibody (#303906 (BioLegend, Inc.))

0.5 μL of APC-labeled CD62a antibody (#304910 (BioLegend, Inc.))

10 μL of FITC-labeled PAC-1 antibody (#304910 (Becton, Dickinson and Company))

The platelets were stimulated by reacting at room temperature after adding PMA (phorbol 12-myristate-13-acetate, #P1585-1MG (Sigma)) at a final concentration of 0.2 μM, ADP (#A2754 (Sigma)) at a final concentration of 20 μM, TRAP-6 (Thrombin receptor activator peptide 6, TFA salt, #H8365 (Bachem)) at a final concentration of 20 μM, collagen (Collagen Reagent HORM, Moriya Sangyo K. K.) at a final concentration of 1 μg/mL or a mixture thereof.

Measurement was carried out using FACS Verse manufactured by Becton Dickinson and Company 30 minutes after the reaction. 400 μL of Tyrode's buffer $Ca^+$ were added immediately before measurement to bring to a total volume of 600 μL. This total volume of 600 μL was used for the FACS measurement sample.

The number of particles positive for CD42a and CD42b were considered to represent the number of platelets, and the ratio of the mean fluorescence intensities (MFI) of PAC-1 and CD62p in this platelet fraction before and after stimulation was calculated.

The results are shown in FIG. 1. The number of platelets bound by PAC-1 and anti-CD62p antibody was confirmed to increase following addition of SR-1, and function was confirmed to be higher than in the case of the absence of SR-1. Based on the results for PAC-1 in particular, SR-1 was used at a concentration of 750 nM in subsequent experiments.

3. Examination of Duration of Overexpression of BMI1 Gene, c-MYC Gene and BCL-xL Gene An experiment was conducted in the same manner as in section 2 by making the period of time from the final day of subculturing in the preparation of immortalized megakaryocytes of section 1 to washing of the cells with PBS(−) to be 1 day, 2 days or 3 days, making the concentration of SR-1 to be 75 nM or 750 nM following completion of overexpression, and making the seeding density to be $1\times10^5$ cells/mL.

Figure 2:
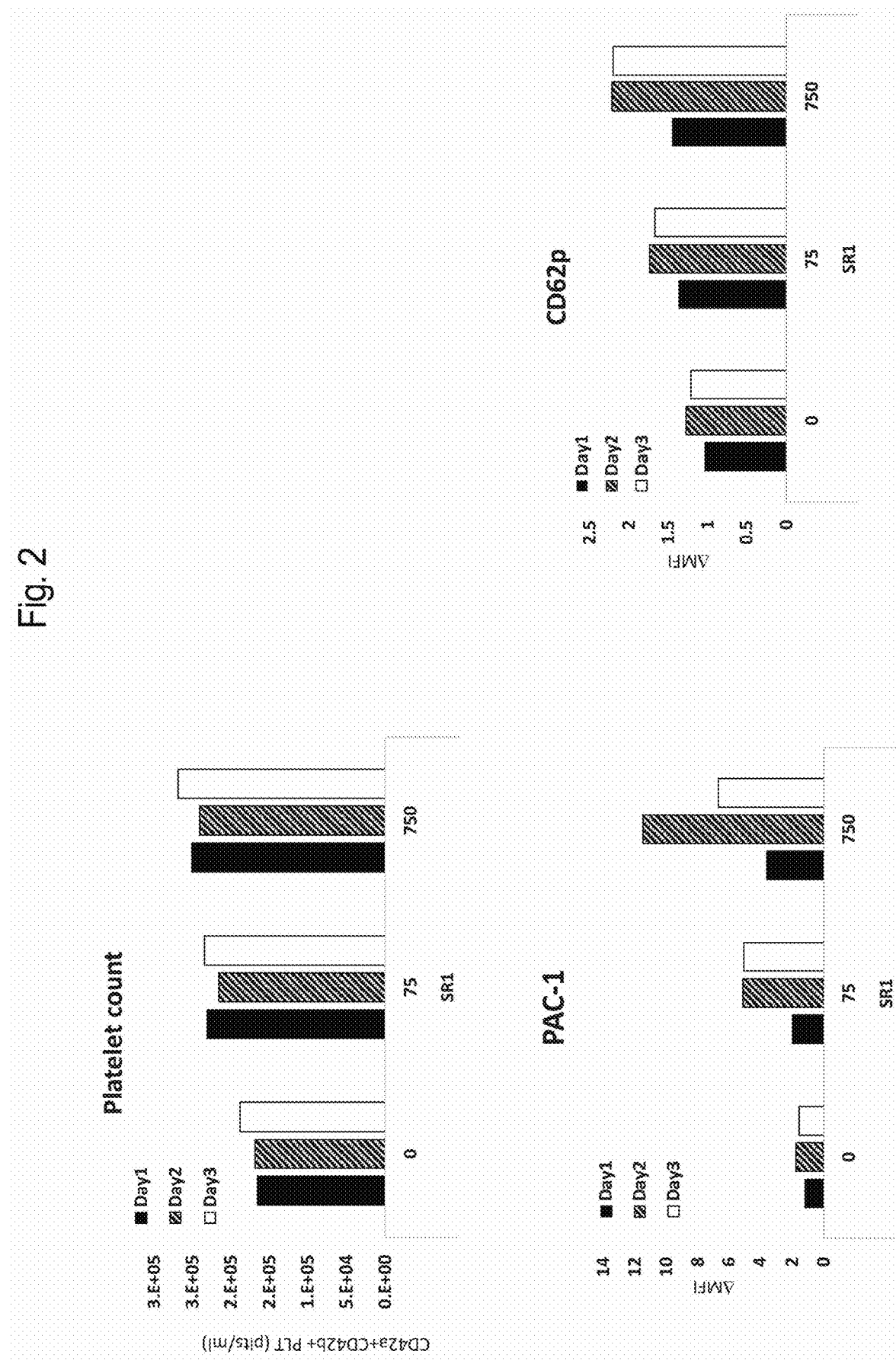
FIG. 2 indicates the results of measuring the number and function of platelets produced when carrying out static culturing following the addition of SR-1 while changing the number of days of culturing following subculturing.

The results are shown in FIG. 2. Although there were hardly any differences observed in the numbers of platelets produced from days 1 to 3 of overexpression, carrying out overexpression for two days or more was observed to result in a tendency towards higher function.

4. Examination of Shake Culturing

An experiment was conducted in the same manner as in sections 2 and 3 with the exception of carrying out shake culturing after having disseminated the cells in an E125 flask instead of a 6-well plate at 25 m L/flask and a seeding density of $1\times10^5$ cells/mL to examine the relationship between SR-1 concentration and seeding density of immortalized megakaryocytes.

The results are shown in FIGS. 3 and 4. Results were obtained that were similar to those of static culturing.

5. Examination of SR-1 Analogues

An experiment was conducted in the same manner as in section 2 with the exception of using analogues of SR-1 as AhR antagonists at the concentrations shown in the diagram.

The results are shown in FIG. 5. The number of platelets produced and the function thereof were confirmed to be enhanced regardless of which AhR antagonist was added. In addition, the results of changing the concentrations of the AhR antagonists are shown in greater detail in FIGS. 6A and 6B.

6. Examination of Effect of Co-addition of AhR Antagonist and ROCK Inhibitor

The effect of adding both SR-1 (AhR antagonist) and Y27632 (ROCK inhibitor) was investigated. Immortalized megakaryocytes obtained according to the method described in section 1 were washed twice with PBS(−) followed by removing the doxycycline to terminate overexpression, static culturing after disseminating the cells in a 6-well plate at 2 mL/well and a seeding density of $1\times10^5$ cells/mL, and then shake culturing in an E125 flask at 25 mL/flask and a seeding density of $1\times10^5$ cells/m L.

The medium was obtained by adding the following components to IMDM serving as the basal medium (concentrations indicate final concentrations).

FBS: 15%
L-glutamine
ITS
MTG
Ascorbic acid
SCF: 50 ng/mL
TOP-like agent: 200 ng/mL
SR-1: 750 nM
Y27632: 10 μM Culturing was implemented under conditions of 37° C., 5% $CO_2$ and 20% $O_2$. The numbers of platelets and PAC-1 positive cells were measured using the same method as described in the above-mentioned section 2.

Figure 7:
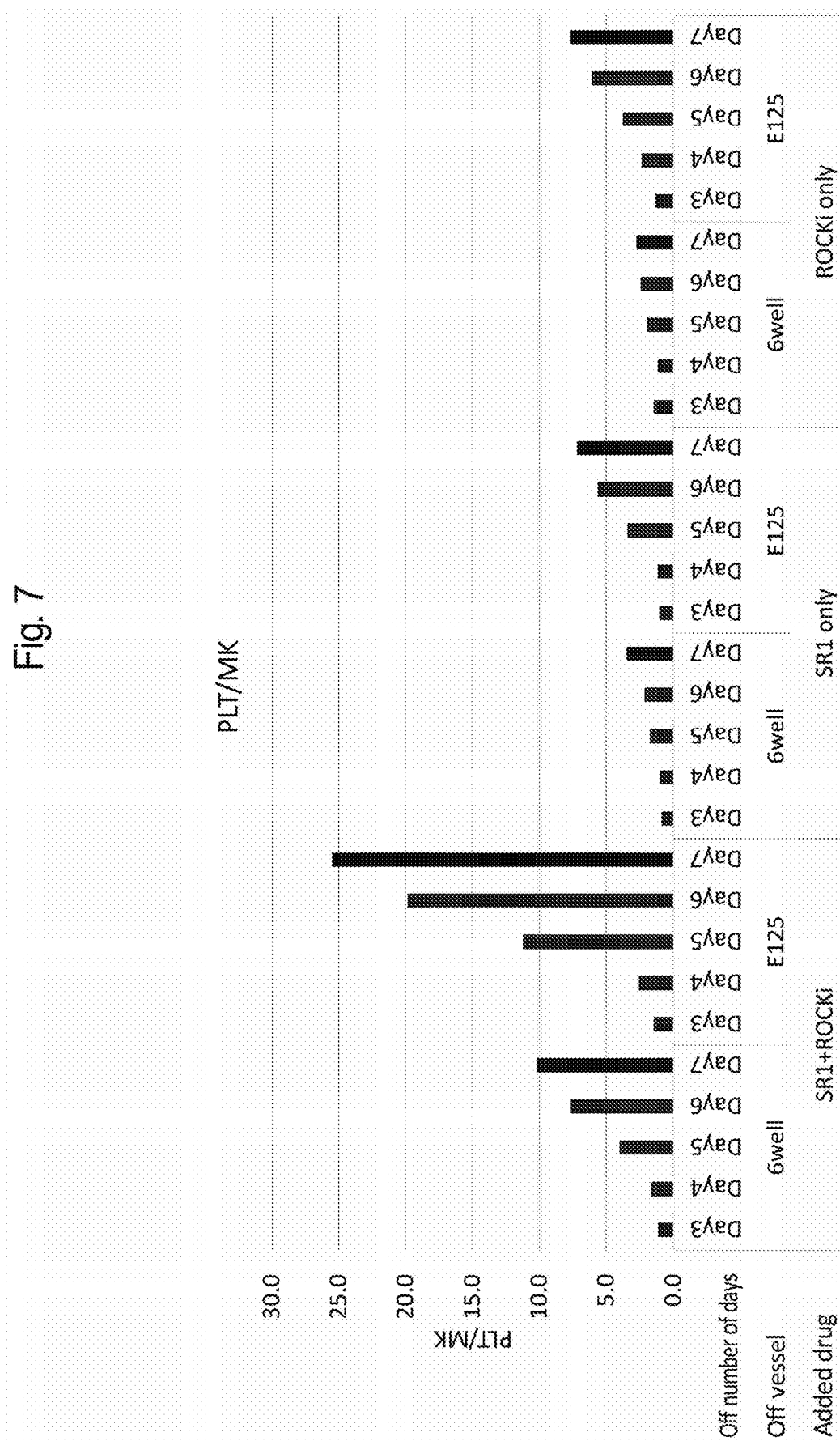
FIG. 7 indicates the results of measuring the number and platelets produced by adding SR-1 alone, Y27632 (ROCK inhibitor) alone or a combination of SR-1 and Y27632 and static culturing (6 wells) or shake culturing (E125) megakaryocytes.
Figure 8:
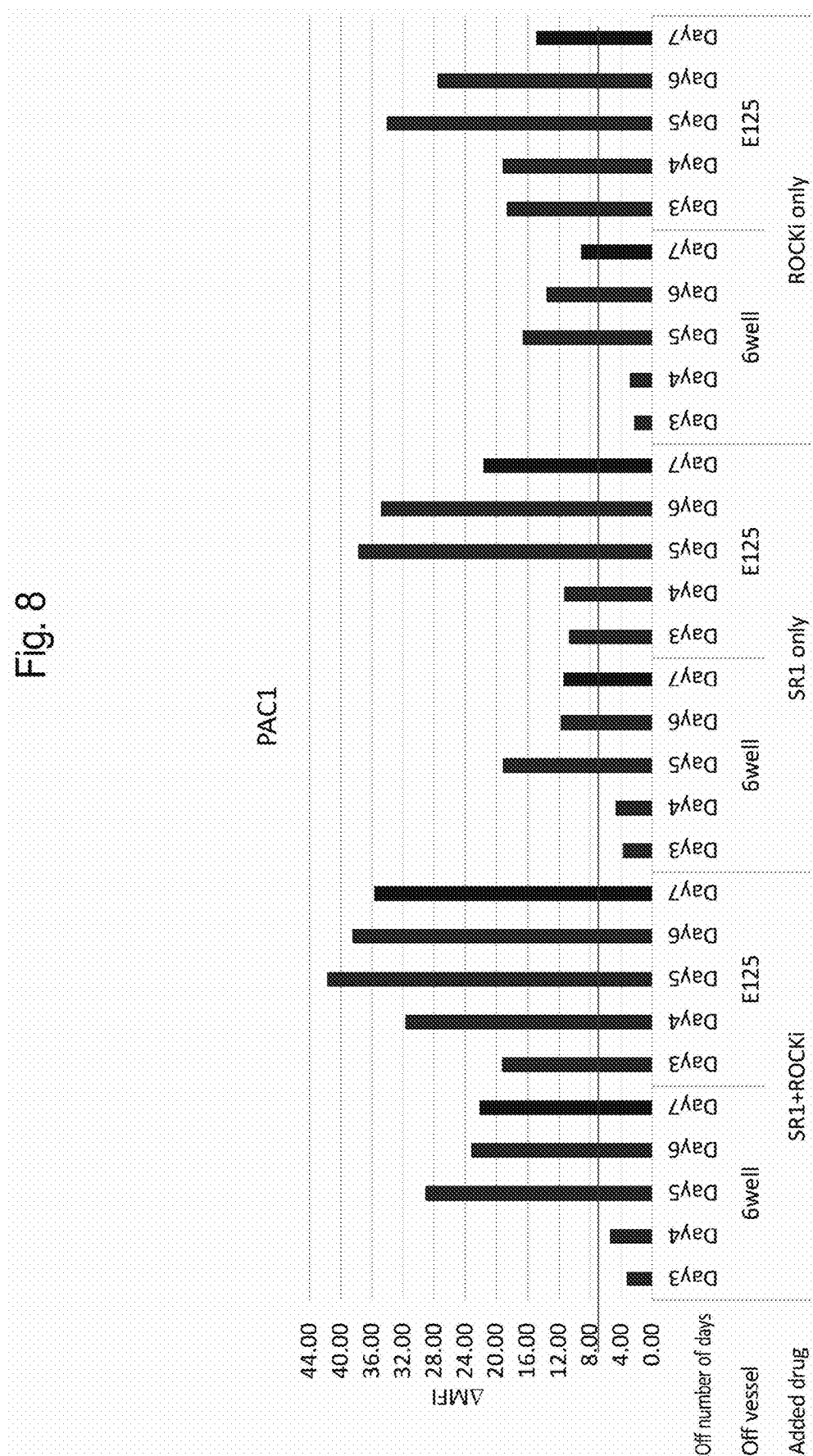
FIG. 8 indicates the results of measuring the function of platelets produced by adding SR-1 alone, Y27632 (ROCK inhibitor) alone or a combination of SR-1 and Y27632 and static culturing (6 wells) or shake culturing (E125) megakaryocytes.
Figure 9:
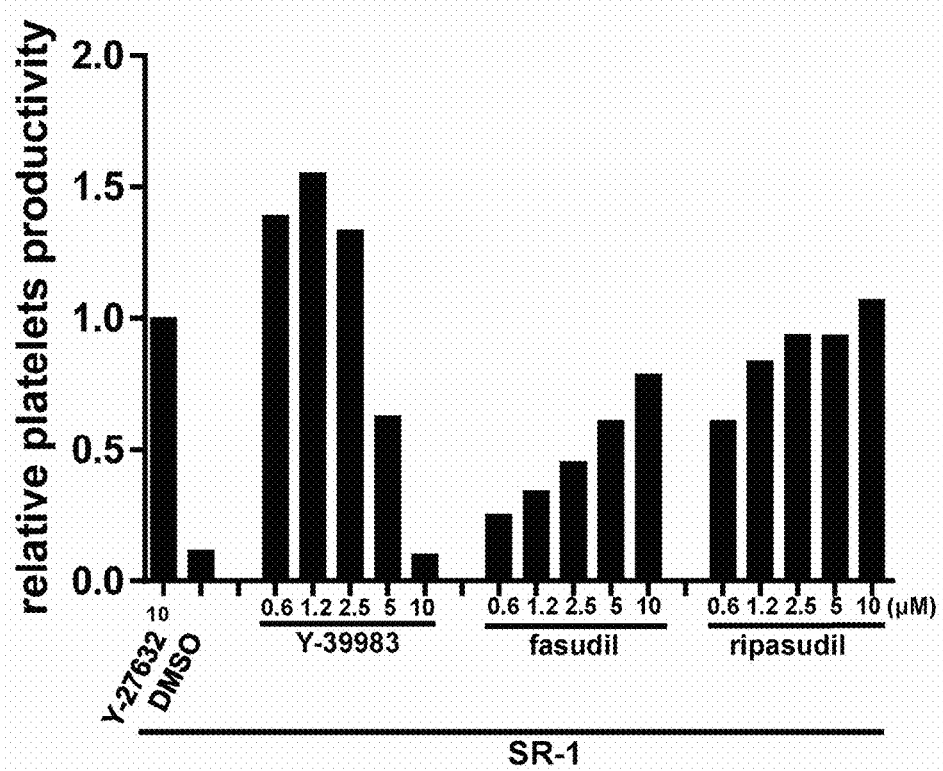
FIG. 9 indicates the results of measuring the number of platelets produced by adding a combination of SR-1 and Y-39983, fasudil hydrochloride or ripasudil (ROCK inhibitors) and shake culturing (E125) megakaryocytes.
Figure 10:
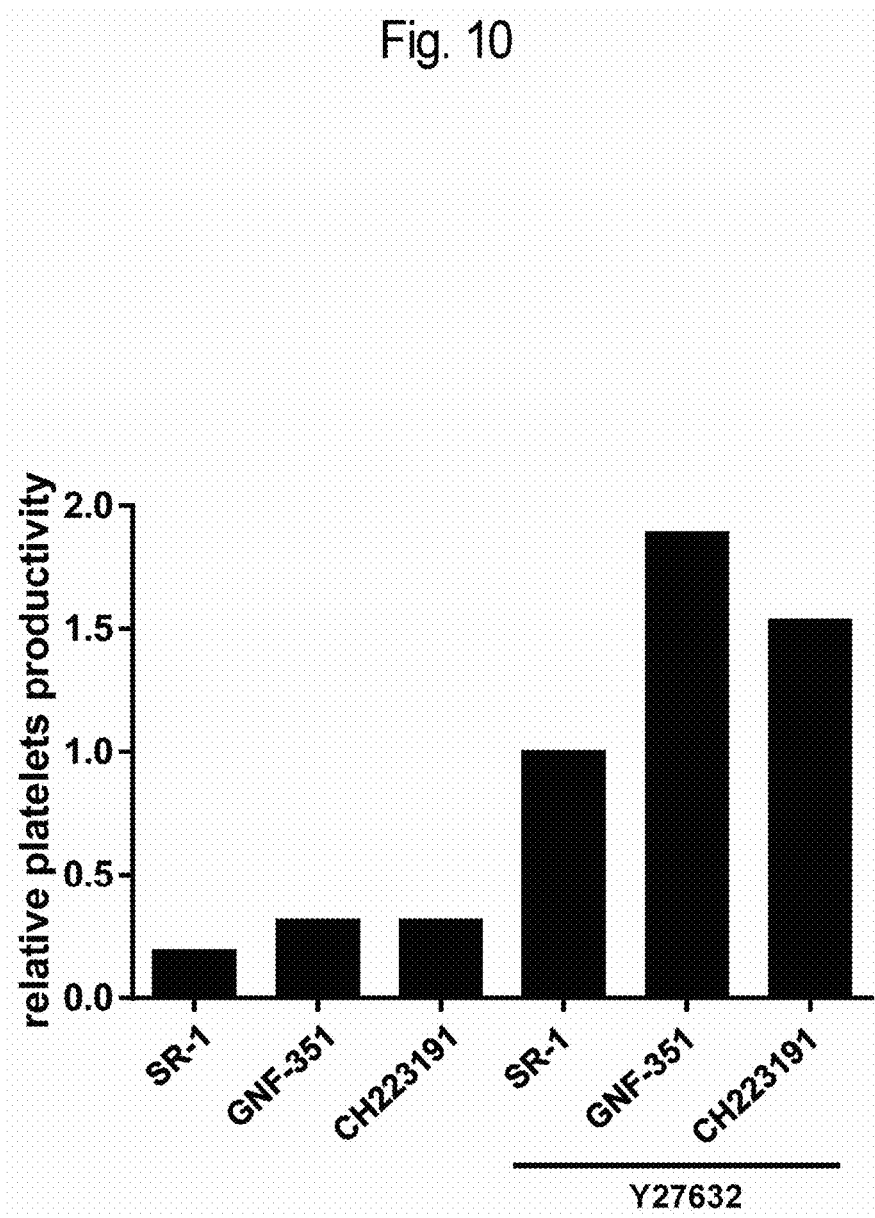
FIG. 10 indicates the results of measuring the number of platelets produced by adding combinations of GNF-351 or CH-223191 (AhR antagonists) and Y27632 (ROCK inhibitor) and shake culturing (E125) megakaryocytes.

The results are shown in FIGS. 7 and 8. Co-addition of SR-1 and Y27632 was confirmed to result in synergistic enhancement of the number and function of the platelets produced in comparison with the case of adding each alone. Similar synergistic effects were confirmed for combinations of SR-1 and other ROCK inhibitors (such as Y39983, fasudil hydrochloride, ripasudil, SLX-2119, RKI-1447, azaindole1 or SR-3677). The results for Y-39983, which demonstrated a prominent synergistic effect that exceeded that of Y27632, are shown in FIG. 9. Fasudil hydrochloride and ripasudil also demonstrated concentration-dependent synergistic effects comparable to that of Y27632. When the number of platelets produced and so forth was subsequently examined for combinations of Y27632 and other AhR antagonists, synergistic effects were observed for all combinations thereof. The results for GNF-351 and CH-223191, which demonstrated prominent synergistic effects that exceeded that of SR-1, are shown in FIG. 10. Although the results are not shown, the combination of GNF-351 and Y-39983 in particular demonstrated a surprisingly prominent effect.

In addition, although the number of platelets produced increased with the number of days of culturing, the number of PAC1-positive functional platelets tended to reach a maximum on about day 5 of addition.

7. Examination of FBS Substitutes

An experiment was conducted in the same manner as that described in the above-mentioned section 2 or 6 with the exception of using 15% human-derived serum (indicated as human serum in the drawing, pooled normal human serum (#12181201 (Kohjin Bio Co., Ltd.))) or 15% human-derived plasma (indicated as human plasma in the drawing, pooled normal human plasma, heparin-treated (#12250210 (Kohjin Bio Co., Ltd.))) instead of 15% FBS to investigate whether or not FBS can be substituted with a human-derived component.

Figure 11:
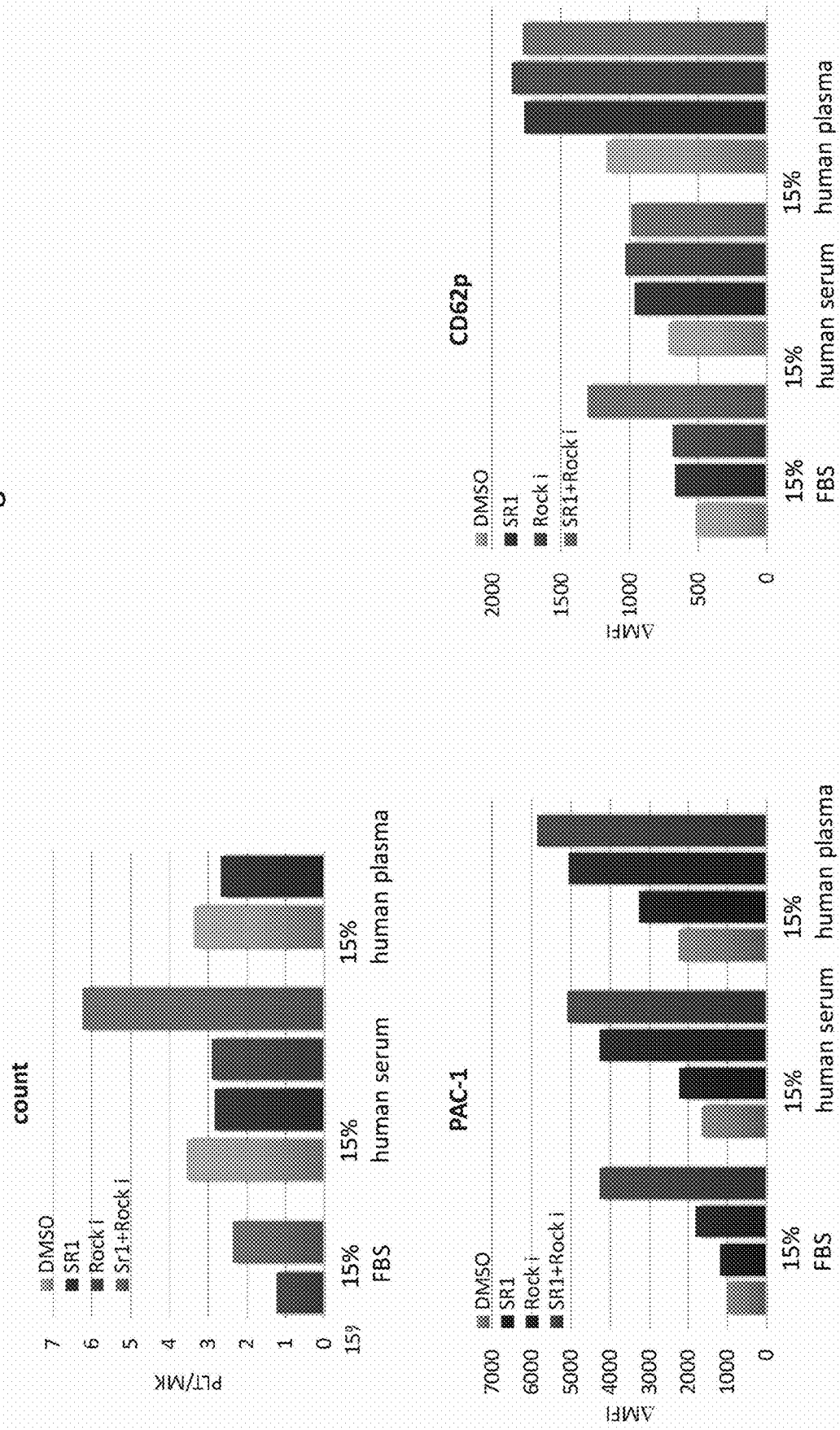
FIG. 11 indicates the number of platelets produced per single megakaryocyte and the proportion of PAC-1-positive platelets or CD62p-positive platelets when megakaryocytes were static-cultured following the addition of 15% human serum or 15% human plasma instead of FBS in the presence of SR-1 alone, in the presence of Y27632 alone, or in the presence of a combination of SR-1 and Y27632.

The results are shown in FIG. 11. Functional platelets were determined to be obtained even if 15% human serum or 15% human plasma is used instead of FBS. Since the use of human serum or human plasma makes it possible to eliminate any components derived from different animal species, platelets can be obtained that have a higher degree of safety.

Next, an experiment was conducted under the same conditions as FIG. 11 with the exception of carrying out shake culturing in the presence of SR-1 and Y27632.

Figure 12:
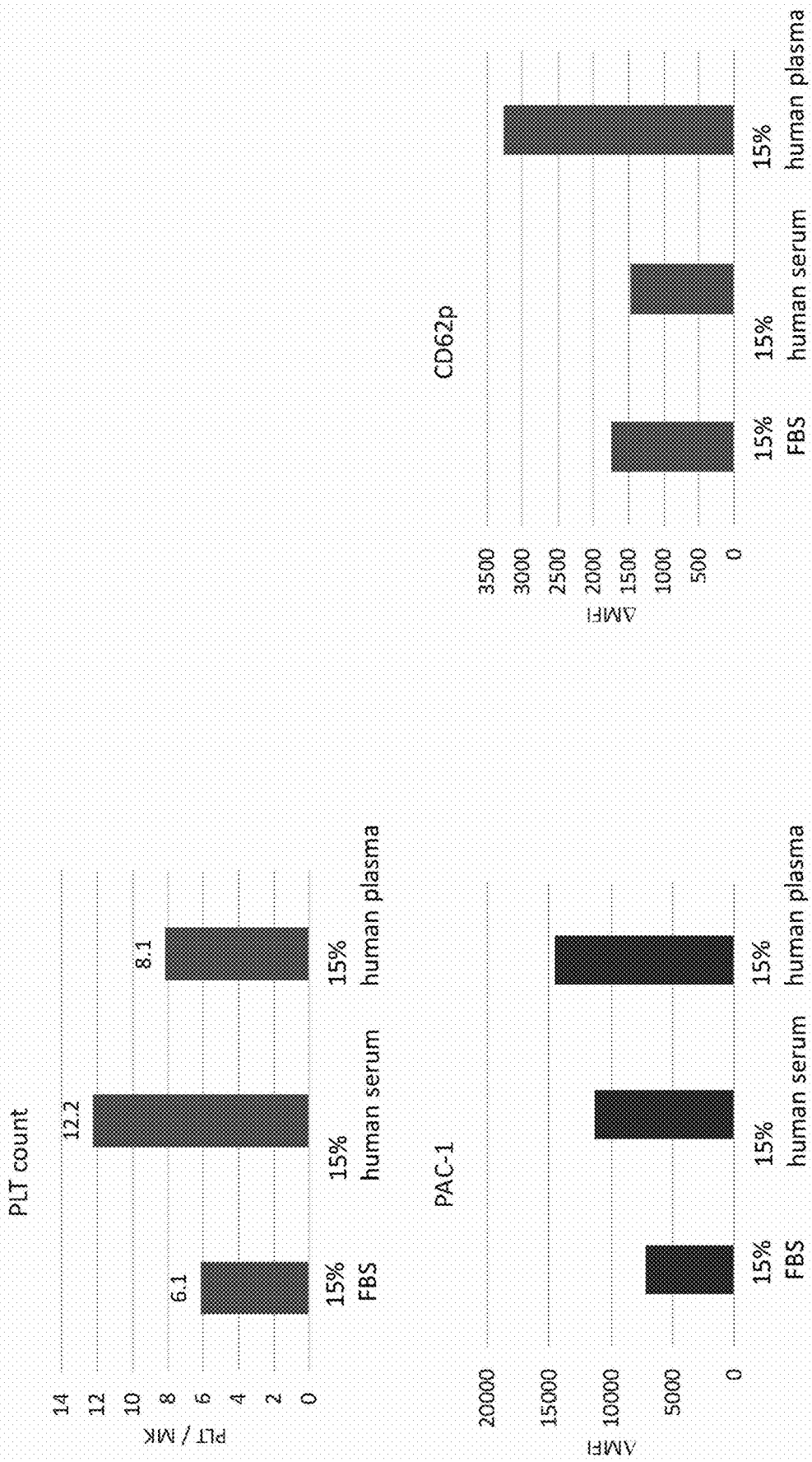
FIG. 12 indicates the number of platelets produced per single megakaryocyte and the proportion of PAC-1-positive platelets or CD62p-positive platelets when megakaryocytes were shake-cultured following the addition of 15% human serum or 15% human plasma instead of FBS in the presence of a combination of SR-1 and Y27632.

The results are shown in FIG. 12. Functional platelets were obtained using 15% human serum and 15% human plasma even in the case of shake culturing instead of static culturing. Shake culturing enables both large-scale culturing and large-scale production.

In general, human plasma is known to be more preferable than human serum for use as a medium additive since the addition of serum to media causes a coagulation reaction resulting in greater susceptibility to differences between lots. Therefore, the concentration dependency of the amount of platelets produced was investigated for human plasma by carrying out shake culturing in the presence of SR-1 and Y27632.

Figure 13:
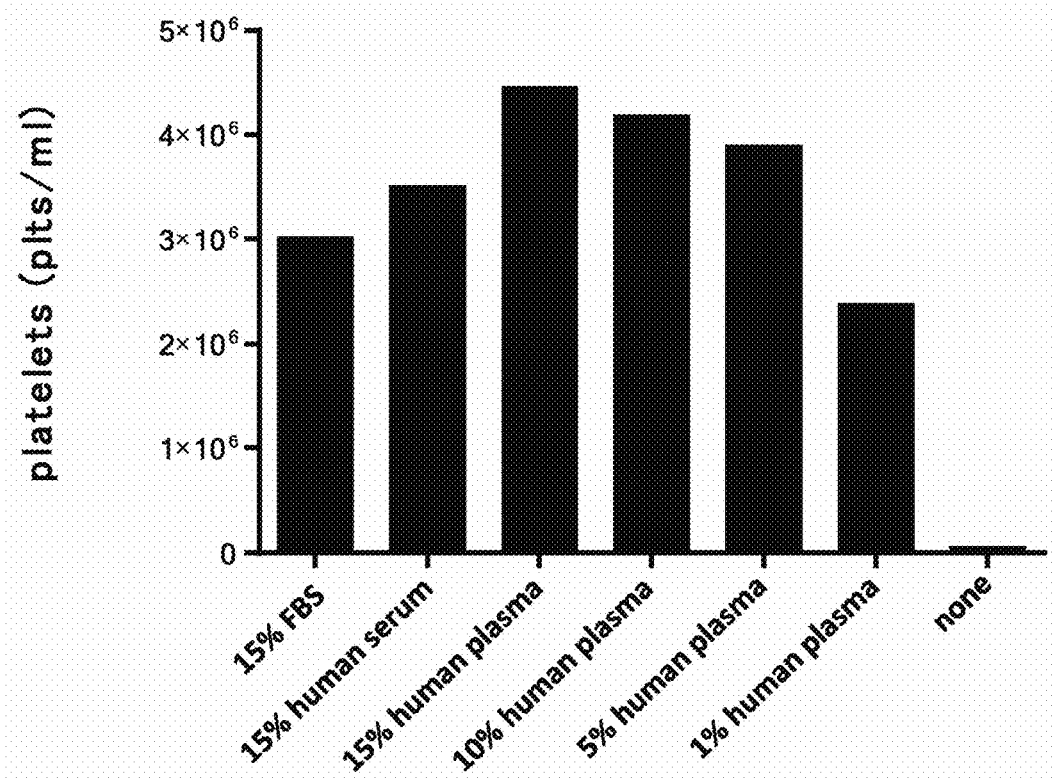
FIG. 13 indicates the results of investigating the dependency of the number of platelets produced on plasma concentration in the presence of a combination of SR-1 and Y27632.

The results are shown in FIG. 13. Although a certain degree of concentration dependency was observed for the amount of platelets produced, an adequate amount of functional platelets was confirmed to able to be obtained even if the plasma concentration was lowered to 1%. Being able to lower human plasma concentration in media makes it possible to reduce the production cost of platelet preparations.

Continuing, a similar experiment was conducted by lowering the concentration of human serum. Static culturing was carried out using citrate-treated pooled normal human plasma (#12250110 (Kohjin Bio Co., Ltd.)) for the human plasma, and pooled normal human serum (#12181201 (Kohjin Bio Co., Ltd.)) for the human serum.

Figure 14:
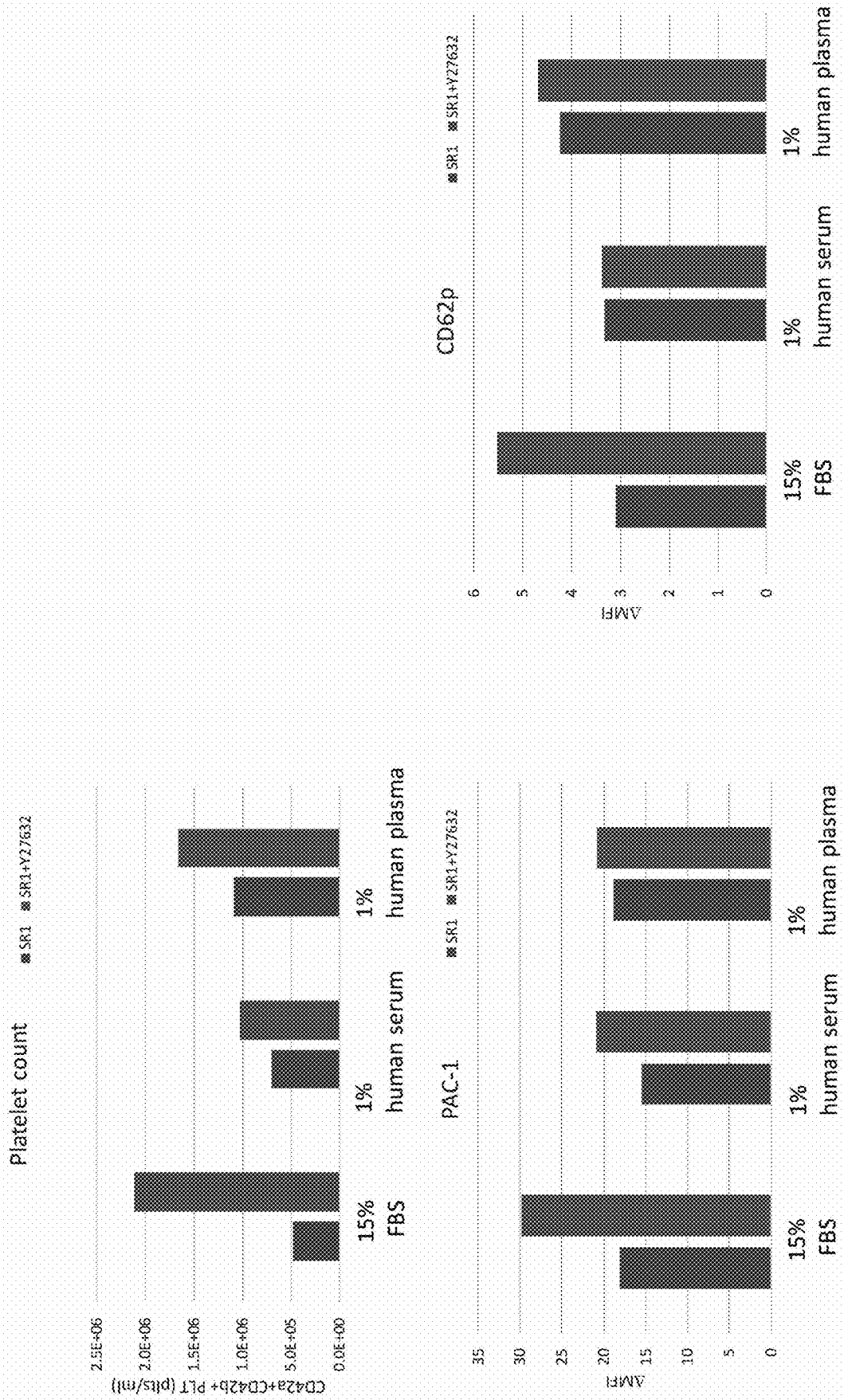
FIG. 14 indicates the number of platelets produced per single megakaryocyte and the proportion of PAC-1-positive platelets or CD62p-positive platelets when megakaryocytes were static-cultured following the addition of 1% human serum or 1% human plasma in the presence of SR-1 alone or in the presence of a combination of SR-1 and Y27632.

The results are shown in FIGS. 14 and 15. An adequate amount of functional platelets was confirmed to be obtained even if the serum concentration was lowered to 1%.

8. Inhibition of HMGA2

Genes of shRUNX1 with GFP, shHMGA2 with GFP and SCRAMBLE with GFP were introduced into the immortalized megakaryocytes prepared in the above-mentioned section 1 using a viral vector. The cells introduced with the above genes (GFP-positive cells) were then sorted. The shRNA used are shown in Table 1 below.

Figure 16:
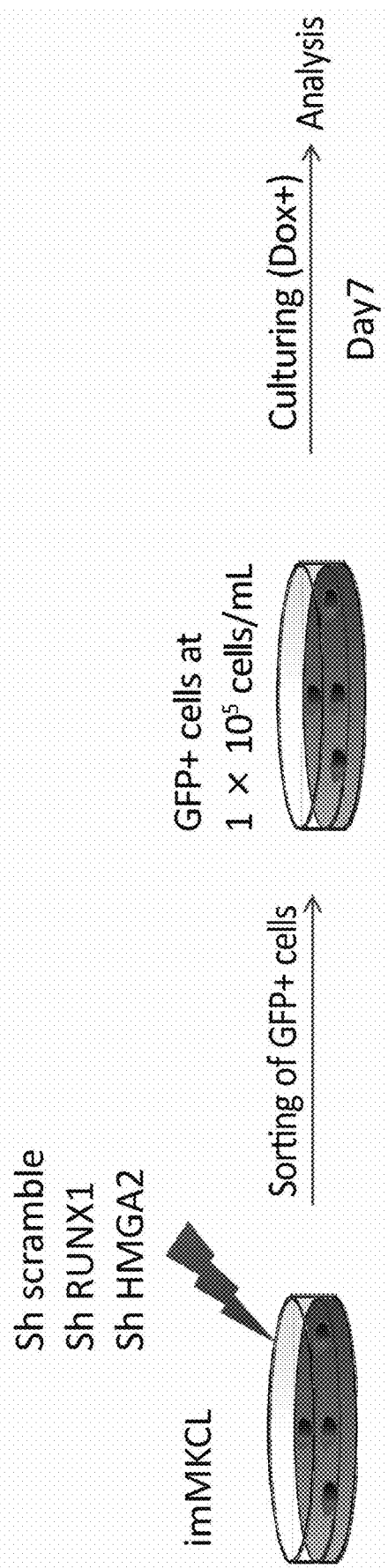
FIG. 16 shows an overview of an experiment including suppressing the expression of HMGA2 gene and RUNX1 gene by shRNA in megakaryocytes immortalized by overexpressing BMI1 gene, c-MYC gene and BCL-xL gene.
Figure 17:
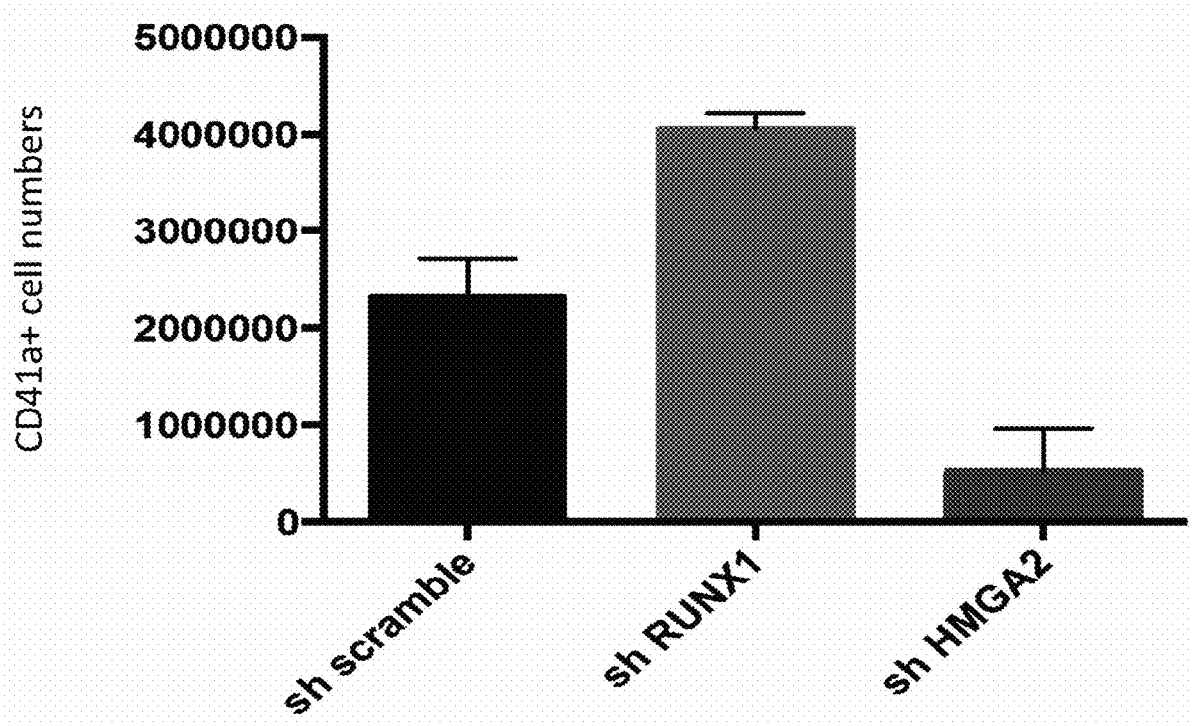
FIG. 17 indicates the results of measuring the number of CD41a-positive cells after culturing megakaryocytes immortalized by overexpression of BMI1 gene, c-MYC gene and BCL-xL gene in the presence of the shRNA shown in FIG. 16.

An overview of the experimental method and the results thereof are shown in FIGS. 16 and 17. Since knockdown of HMGA2 resulted in a decrease in the number of CD41a-positive cells, HMGA2 was determined to be a factor required for self-replication of megakaryocytes prior to multinucleation during the growth phase. On the other hand, since knockdown of RUNX1 resulted in an increase in the number of CD41a-positive cells, RUNX1 was thought to slightly inhibit the growth of megakaryocytes prior to multinucleation.

Figure 18:
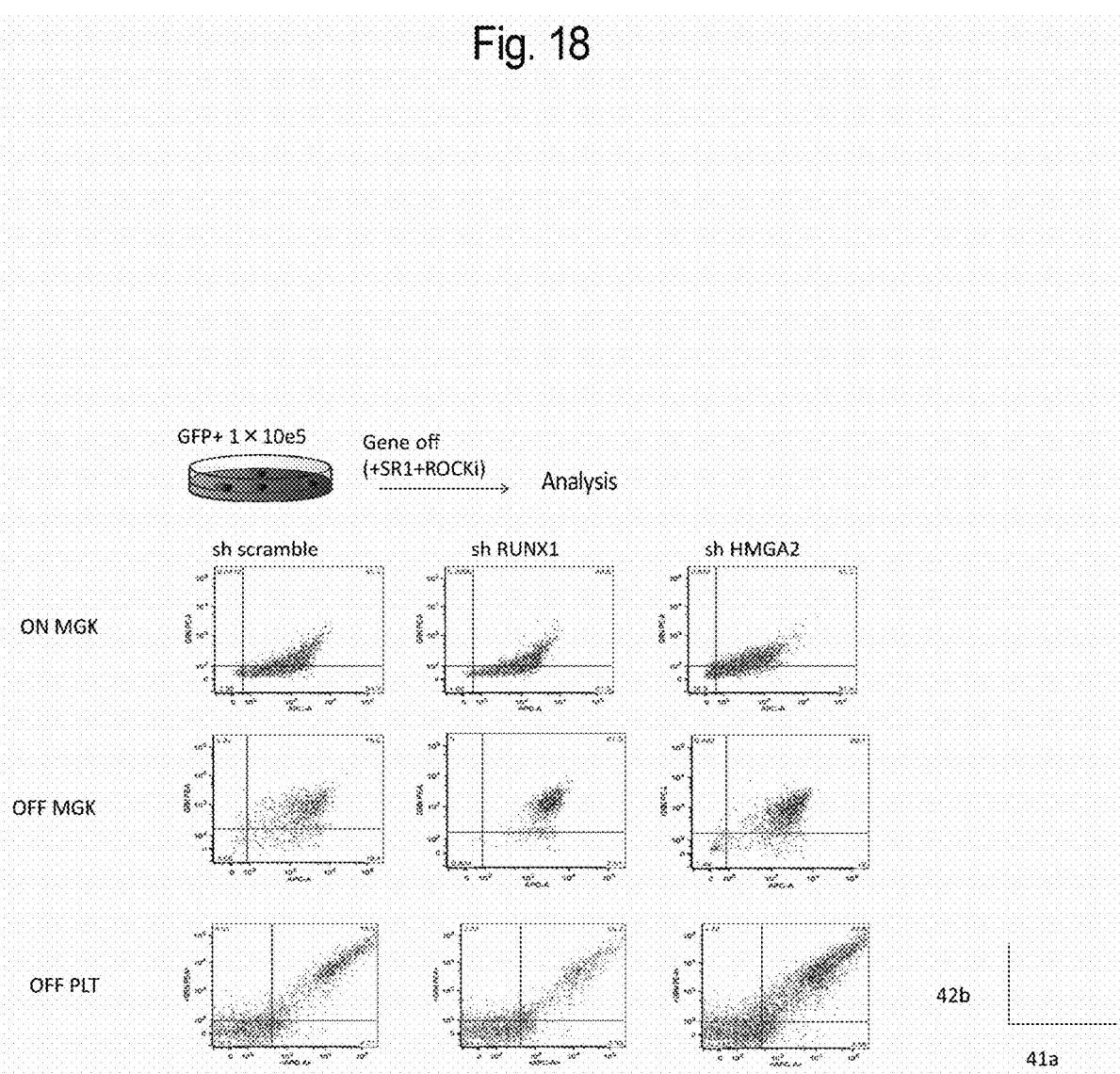
FIG. 18 indicates the results of carrying out flow cytometry using anti-CD42b antibody and anti-41a antibody on megakaryocytes and platelets before and after terminating overexpression of BMI1 gene, c-MYC gene and BCL-xL gene.
Figure 19:
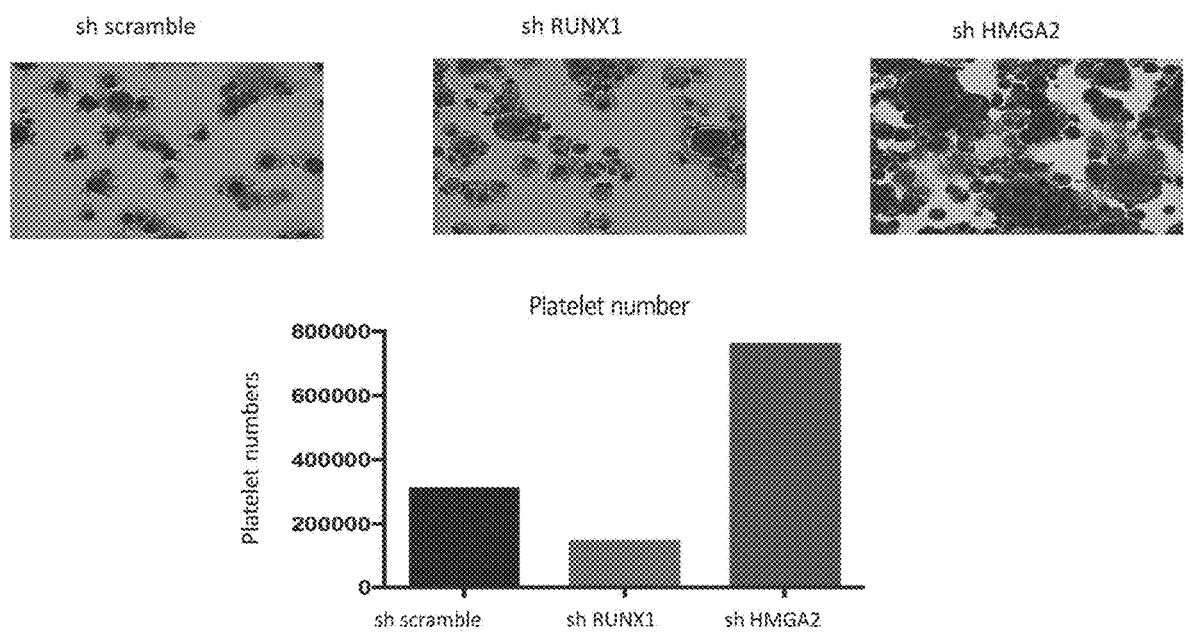
FIG. 19 indicates the results of observing the status of megakaryocytes (top) and measuring the number of platelets produced (bottom) when megakaryocytes were cultured after terminating overexpression of BMI1 gene, c-MYC gene and BCL-xL gene.

Next, the production of platelets was measured after having terminated overexpression of cMYC, BMI1 and BCL-xL genes using the method described in the aforementioned section 1-5. The results are shown in FIGS. 18 and 19.

As shown in the drawings, the content of megakaryocytes positive for CD41a and CD42b increased after terminating overexpression (OFF MGK) in comparison with prior to terminating overexpression (ON MGK), and platelets positive for CD41a and CD42b were confirmed to be produced in large amounts. As shown in the top part of FIG. 19, knockdown of HMGA2 results in considerable promotion of megakaryocyte multinucleation, and as shown in the bottom part of FIG. 19, the number of platelets produced per megakaryocyte was confirmed to increase dramatically.

9. Effects of HMGA2 Inhibition, AhR Antagonists and ROCK Inhibitors

Genes of shRUNX1 with GFP, shHMGA2 with GFP and shSCRAMBLE with GFP were introduced into the immortalized megakaryocytes prepared in the previous section 1 in the same manner as section 8 above, and after adding megakaryocyte medium containing 1 μg/mL of doxycycline (DOX) (namely, IMDM containing 15% FBS, L-glutamine, ITS, MTG, ascorbic acid, 50 ng/mL SCF and 50 ng/mL TPO) and culturing for 7 days, the cells introduced with the above-mentioned genes (GFP-positive cells) were isolated by sorting. $1 \times 10^5$ isolated cells introduced with shHMGA2 were disseminated in a 6-well plate and cultured for 7 days in DOX-free megakaryocyte medium (namely, medium for interrupting expression of exogenous genes) in the absence of any addition, after adding only 750 nM SR-1, after adding only 10 μM Y27632 or after adding 750 nM SR-1 and 10 μM Y27632.

On the other hand, isolated cells introduced with shRUNX1 and shSCRAMBLE were cultured for 7 days in DOX-free megakaryocyte medium containing 750 nM SR-1 and 10 μM Y27632. The resulting cells were adhered to a slide glass using Cytospin and observed with an electron microscope (top of FIG. 20).

Figure 20:
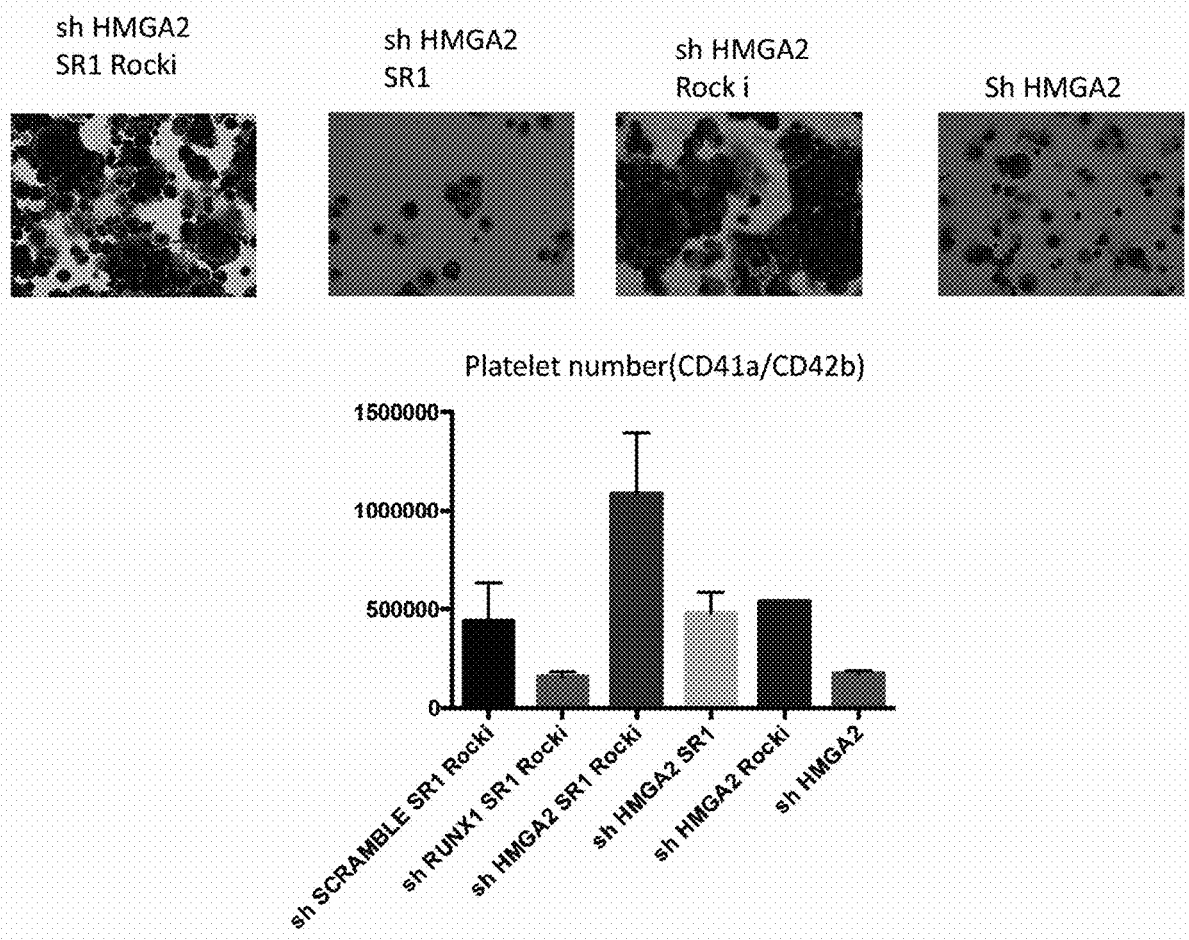
FIG. 20 indicates the results of observing the status of megakaryocytes (top) and the number of platelets produced per unit cells ($1 \times 10^5$ cells) (bottom) when megakaryocytes introduced with siRNA against HMGA2 and RUNX1 or a control (indicated as shHMGA2, shRUNX1 and shSCRAMBLE, respectively) were cultured in the presence or absence of addition of SR-1 and/or ROCK inhibitor after terminating overexpression of BMI1 gene, c-MYC gene and BCL-xL gene. In the drawing, SR-1 refers to the addition of SR-1 while ROCKi refers to the addition of Y27632.

In addition, platelets (CD41a-positive, CD42b-positive) present in the culture supernatants were measured using FACS (bottom of FIG. 20). As a result, multinucleated and

TABLE 1

| Name | Target Sequence | shRNA Sequence |
|---|---|---|
| shSCRAMBLE | GAGGTCACACTAGAGAGTTATA (SEQ ID NO: 1) | gatccccGAGGTCACACTAGAGAGTTATA ttcaagagaTATAACTCTCTAGTGTGACCTC tttttggaaaa (SEQ ID NO: 2) |
| shRUNX1 | ACTTTCCAGTCGACTCTCA (SEQ ID NO: 3) | gatccccACTTTCCAGTCGACTCTCA ttcaagagaTGAGAGTCGACTGGAAAGT tttttggaaaa (SEQ ID NO: 4) |
| shHMGA2 | ATGAGACGAAATGCTGATGTAT (SEQ ID NO: 5) | gatccccATGAGACGAAATGCTGATGTAT ttcaagagaATACATCAGCATTTCGTCTCAT tttttggaaaa (SEQ ID NO: 6) | enlarged cells were observed as a result of culturing megakaryocytes subjected to HMGA2 knockdown in medium containing an AhR antagonist and ROCK inhibitor, and the number of platelets produced per unit cell was confirmed to increase considerably. In addition, platelet production efficiency was confirmed to become even higher in the case of combining an AhR antagonist and ROCK inhibitor.

10. HMGA2 Inhibition and Megakaryocyte Maturation

Cells introduced with genes shRUNX1, shHMGA2 and shSCRAMBLE obtained in section 9 above were cultured in DOX-free megakaryocyte medium containing SR-1 and Y27632 and observed with an electron microscope.

Figure 21:
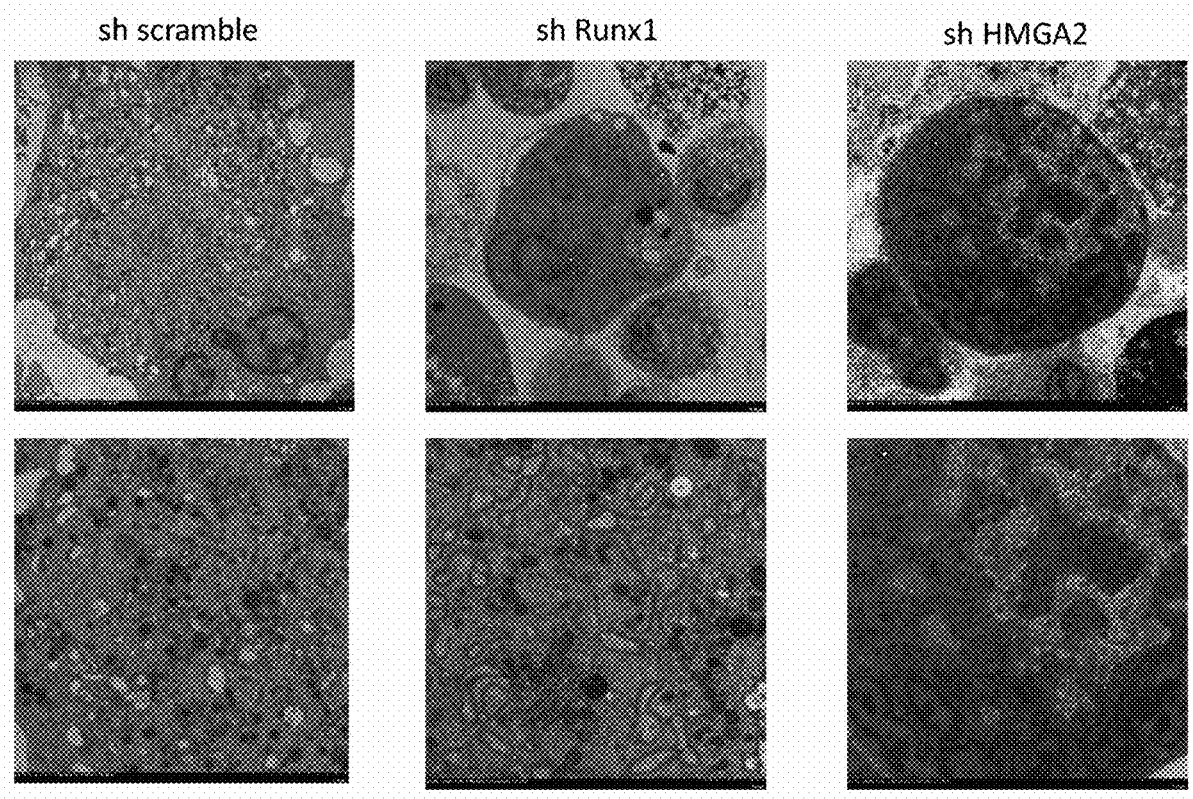
FIG. 21 depicts electron micrographs of megakaryocytes introduced with siRNA against HMGA2 and RUNX1 or a control (indicated as shHMGA2, shRUNX1 and shSCRAMBLE, respectively) that were cultured after adding SR-1 and a ROCK inhibitor following termination of overexpression of BMI1 gene, c-MYC gene and BCL-xL gene. The bottom row of micrographs depicts enlarged views of the top row of micrographs.

The results are shown in FIG. 21. As a result, in the case of having introduced shRUNX1, there were numerous small nucleated cells, development of demarcation membrane systems (DMS) in the cells was lacking, and secretory granules were confirmed to only be formed to a moderate degree. Similarly, in the case of having introduced shSCRAMBLE, there were numerous small nucleated cells, development of DMS in the cells was lacking, and there was confirmed to be hardly any formation of secretory granules. On the other hand, in the case of having introduced shHMGA2, multinucleated and enlarged cells were observed and the formation of a DMS and secretory granules was observed in these cells.

On the basis of the above results, it was suggested that inhibition of HMGA2 in megakaryocytes makes it possible to enhance platelet production efficiency, the resulting megakaryocytes become multinucleated and enlarged in the same manner as megakaryocytes in the body as a result of combining an AhR antagonist and ROCK inhibitor, the megakaryocytes mature to a degree that the formation of DMS and secretory granules is observed, and platelet production efficiency becomes even higher as a result thereof.

SEQUENCE LISTING FREE TEXT

SEQ ID NO: 1 indicates the target sequence of shSCRAMBLE.
SEQ ID NO: 2 indicates the DNA sequence of shSCRAMBLE.
SEQ ID NO: 3 indicates the target sequence of shRUNX1.
SEQ ID NO: 4 indicates the DNA sequence of shRUNX1.
SEQ ID NO: 5 indicates the target sequence of shHMGA2.
SEQ ID NO: 6 indicates the DNA sequence of shHMGA2.

What is claimed is:

1. A platelet production promoting agent which comprises one or a plurality of aryl hydrocarbon receptor (AhR) antagonists selected from the group consisting of 4-(2-(2-(benzo[b]thiophen-3-yl)-9-isopropyl-9H-purin-6-ylamino) ethyl)phenol (SR-1), 2-methyl-2H-pyrazole-3-carboxylic acid (2-methyl-4-o-tolylazo-phenyl)-amide (CH-223191), and N-]2-(3H-indol-3-yl)ethyl]-9-isopropyl-2-(5-methyl-3-pyridyl)purin-6-amine (GNF-351), and one or a plurality of Rho-associated coiled-coil forming kinase (ROCK) inhibitors selected from the group consisting of Y27632 and Y39983.

2. The platelet production promoting agent according to claim 1, wherein the AhR antagonist is GNF-351 and the ROCK inhibitor is, Y39983.

3. A platelet production method, which comprises a step for bringing the platelet production promoting agent according to claim 1 into contact with megakaryocytes or progenitor cells thereof.

4. The method according to claim 3, wherein the contact step is carried out under conditions of not using feeder cells.

5. The method according to claim 4, which is carried out under shake culturing conditions.

6. The method according to claim 3, further comprising a step for suppressing the expression or function of high mobility group At-hook (HMGA) proteins in the megakaryocytes or progenitor cells thereof by siRNA or miRNA that directly or indirectly suppresses expression of HMGA gene.

7. The method according to claim 3, wherein the megakaryocytes are cells obtained by overexpressing at least one gene selected from the group consisting of a cancer gene, polycomb gene and apoptosis suppressor gene in cells less differentiated than the megakaryocytes, followed by terminating the overexpression.

8. The method according to claim 7, wherein the cells less differentiated than the megakaryocytes are hematopoietic progenitor cells produced from pluripotent stem cells.

9. The method according to claim 3, further comprising a step for recovering platelets from the megakaryocytes.

10. A platelet production method, which comprises bringing a platelet production promoting agent comprising (a) one or a plurality of aryl hydrocarbon receptor (AhR) antagonists and (b) one or a plurality of Rho-associated coiled-coil forming kinase (ROCK) inhibitors selected from the group consisting of Y27632, Y39983, SLX-2119, RKI-1447, azaindole1, SR-3677, and Staurosporine into contact with megakaryocytes or progenitor cells thereof, and suppressing the expression or function of high mobility group At-hook (HMGA) proteins in the megakaryocytes or progenitor cells thereof by siRNA or miRNA that directly or indirectly suppresses expression of HMGA gene.

11. The method according to claim 10, wherein the contact step is carried out without the use of feeder cells.

12. The method according to claim 10, which is carried out under shake culturing conditions.

13. The method according to claim 10, wherein the megakaryocytes are cells obtained by overexpressing at least one gene selected from the group consisting of a cancer gene, polycomb gene and apoptosis suppressor gene in cells less differentiated than the megakaryocytes, followed by terminating the overexpression.

14. The method according to claim 10, further comprising a step for recovering platelets from the megakaryocytes.

15. A composition, which comprises
(a) 200 nM to less than 1000 nM of 4-(2-(2-(benzo[b]thiophen-3-yl)-9-isopropyl-9H-purin-6-ylamino)ethyl) phenol (SR-1),
0.2 µM to less than 4 µM of 2-methyl-2H-pyrazole-3-carboxylic acid (2-methyl-4-o-tolylazo-phenyl)-amide (CH-223191), or
20 nM to less than 300 nM of N42-(3H-indol-3-yl) ethyl]-9-isopropyl-2-(5-methyl-3-pyridyl)purin-6-amine (GNF-351); and
(b) one or a plurality of Rho-associated coiled-coil forming kinase (ROCK) inhibitors selected from the group consisting of Y27632, Y39983, SLX-2119, RKI-1447, azaindole1, SR-3677, and Staurosporine.

16. A platelet production method, which comprises a step for bringing the platelet production promoting agent according to claim 15 into contact with megakaryocytes or progenitor cells thereof.

17. The method according to claim 16, wherein the contact step is carried out under conditions of not using feeder cells.

18. The method according to claim 17, which is carried out under shake culturing conditions.

19. The method according to claim 16, further comprising a step for suppressing the expression or function of high mobility group At-hook (HMGA) proteins in the megakaryocytes or progenitor cells thereof by siRNA or miRNA that directly or indirectly suppresses expression of HMGA gene.

20. The method according to claim 16, further comprising a step for recovering platelets from the megakaryocytes.

\* \* \* \* \*